US010117566B2

(12) United States Patent
Kubo

(10) Patent No.: US 10,117,566 B2
(45) Date of Patent: Nov. 6, 2018

(54) DRIVING FORCE TRANSMISSION MECHANISM FOR MEDICAL DEVICES

(71) Applicant: OLYMPUS CORPORATION, Tokyo (JP)

(72) Inventor: Takafumi Kubo, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/494,621

(22) Filed: Apr. 24, 2017

(65) Prior Publication Data

US 2017/0224195 A1    Aug. 10, 2017

Related U.S. Application Data

(63) Continuation of application No. PCT/JP2016/059914, filed on Mar. 28, 2016.

(30) Foreign Application Priority Data

Jul. 15, 2015    (JP) .................. 2015-141233

(51) Int. Cl.
*A61B 1/06*    (2006.01)
*A61B 1/00*    (2006.01)
(Continued)

(52) U.S. Cl.
CPC ........ *A61B 1/00133* (2013.01); *A61B 1/0016* (2013.01); *A61B 1/00041* (2013.01);
(Continued)

(58) Field of Classification Search
CPC ............ A61B 1/00133; A61B 1/00041; A61B 1/0051; A61B 1/04; A61B 1/06
(Continued)

(56) References Cited

U.S. PATENT DOCUMENTS 1,614,992 A * 1/1927 Roberts .................. F16C 35/06
475/246
2,203,292 A * 6/1940 Best ......................... F16H 1/14
475/230
(Continued)

FOREIGN PATENT DOCUMENTS

JP            5458224 B1    4/2014
WO    WO 2014/045980 A1    3/2014
(Continued)

OTHER PUBLICATIONS

International Search Report dated Jun. 28, 2016 issued in PCT/JP2016/059914.
(Continued)

*Primary Examiner* — William C Joyce
(74) *Attorney, Agent, or Firm* — Scully, Scott, Murphy & Presser, P.C.

(57) ABSTRACT

A driving force transmission mechanism for medical devices, includes a tubular portion including: an opening edge portion which allows a support portion of a drive shaft to be supported at an output end in a state where at least a part of the output end is accommodated in the tubular portion; and a first adjustment section which is configured to fix a gear train in a state where the drive shaft is inserted into the tubular portion and a distal portion of the drive shaft is arranged at a predetermined position where a driven portion is able to be driven and a state where a position of the output end of the gear train is adjusted relative to a position of the support portion of the drive shaft.

14 Claims, 19 Drawing Sheets

(51) Int. Cl.
*A61B 1/005* (2006.01)
*A61B 1/015* (2006.01)
*A61B 1/04* (2006.01)
*G02B 23/24* (2006.01)
*H04N 5/225* (2006.01)

(52) U.S. Cl.
CPC .......... *A61B 1/0051* (2013.01); *A61B 1/0052* (2013.01); *A61B 1/015* (2013.01); *A61B 1/04* (2013.01); *A61B 1/06* (2013.01); *G02B 23/2469* (2013.01); *G02B 23/2476* (2013.01); *H04N 5/2256* (2013.01); *A61B 1/0057* (2013.01); *H04N 2005/2255* (2013.01)

(58) Field of Classification Search
USPC .............. 74/395–397, 400, 401, 409; 464/52
See application file for complete search history.

(56) References Cited

U.S. PATENT DOCUMENTS

| | | | | |
|---|---|---|---|---|
| 3,213,700 A | * | 10/1965 | Brownyer | F16H 1/145 74/424 |
| 4,311,063 A | * | 1/1982 | Sistare | B24B 23/028 74/395 |
| 5,806,371 A | * | 9/1998 | Hibbler | F16H 48/08 475/230 |
| 2010/0203975 A1 | * | 8/2010 | Yaksic | B23B 45/005 464/52 |
| 2014/0330079 A1 | | 11/2014 | Ishizaki et al. | |
| 2016/0196191 A1 | | 7/2016 | Naito | |

FOREIGN PATENT DOCUMENTS

WO  WO 2014/192537 A1  12/2014
WO  WO 2015/072233 A1   5/2015

OTHER PUBLICATIONS

English translation of the Written Opinion of the International Searching Authority from International Application No. PCT/JP2016/059914 dated Aug. 17, 2017.
Extended Supplementary European Search Report dated Jun. 12, 2018 received in European Patent Application No. 16 82 4109.9.
Chinese Office Action dated May 28, 2018 recieved in 20168003408.1.

* cited by examiner

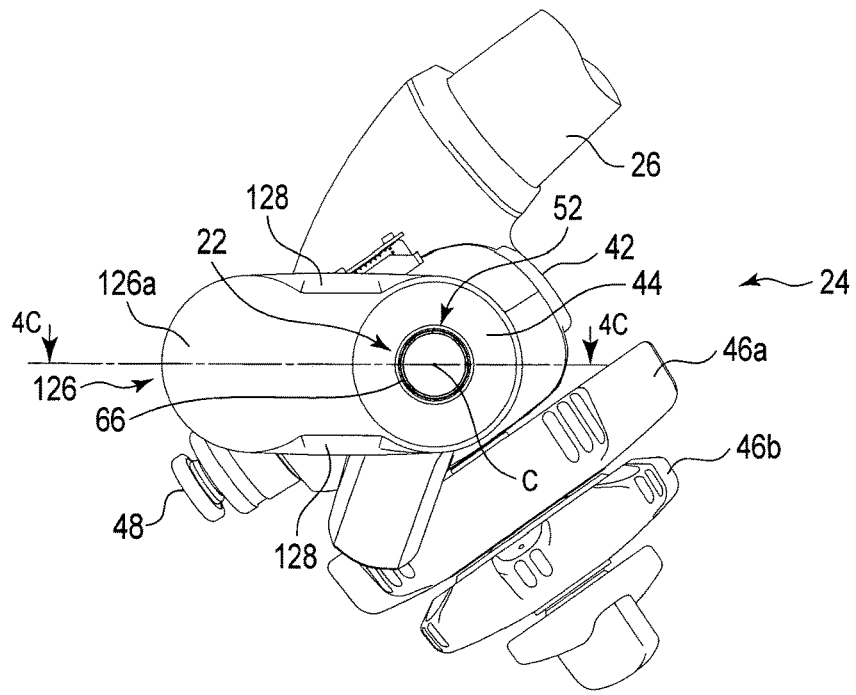
F I G. 4A
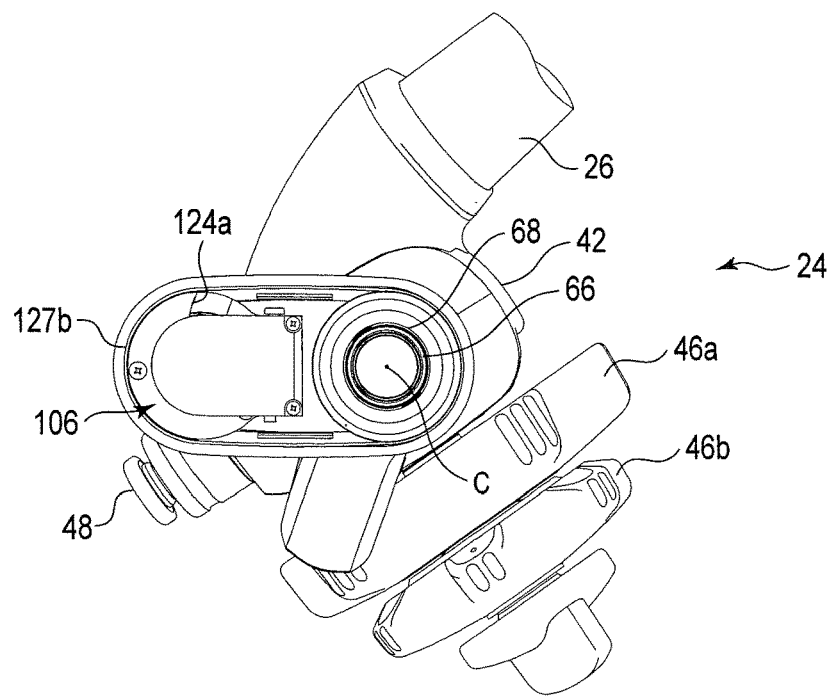
F I G. 4B

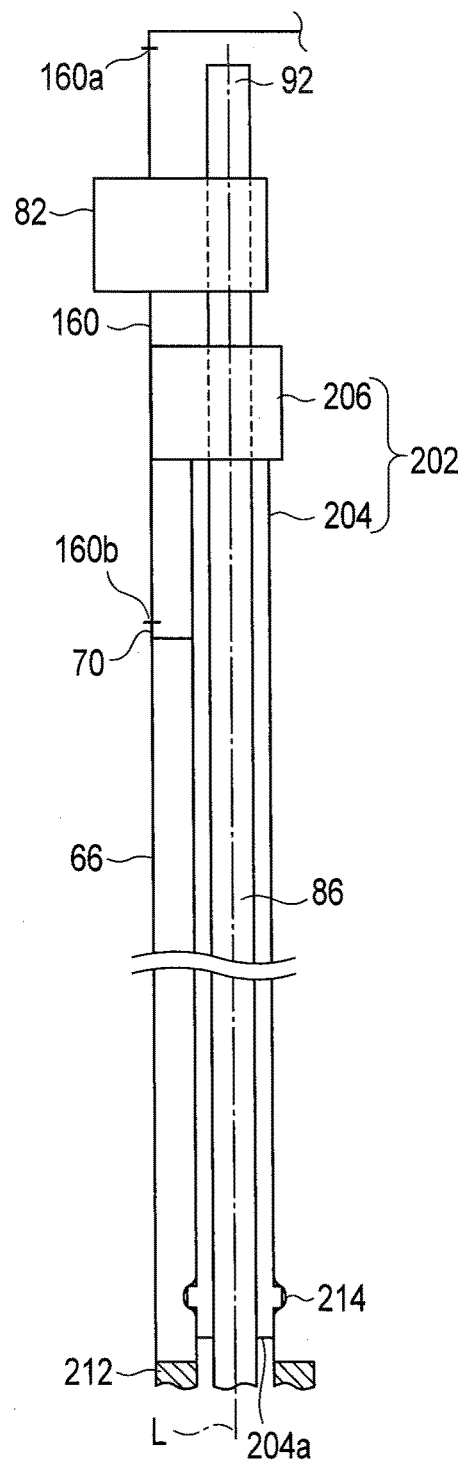
F I G. 10A

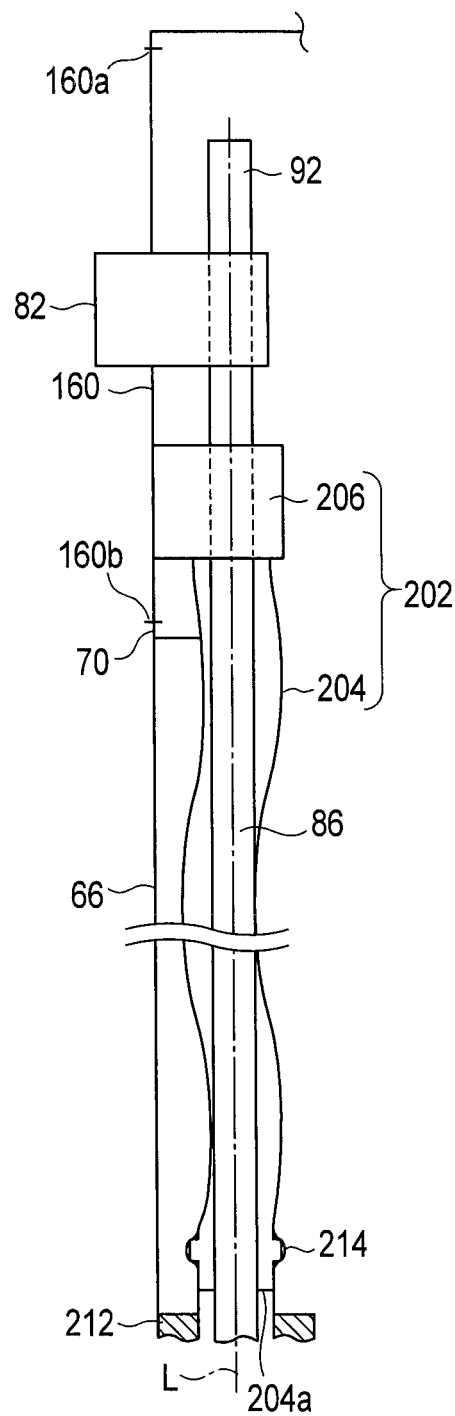
F I G. 11B

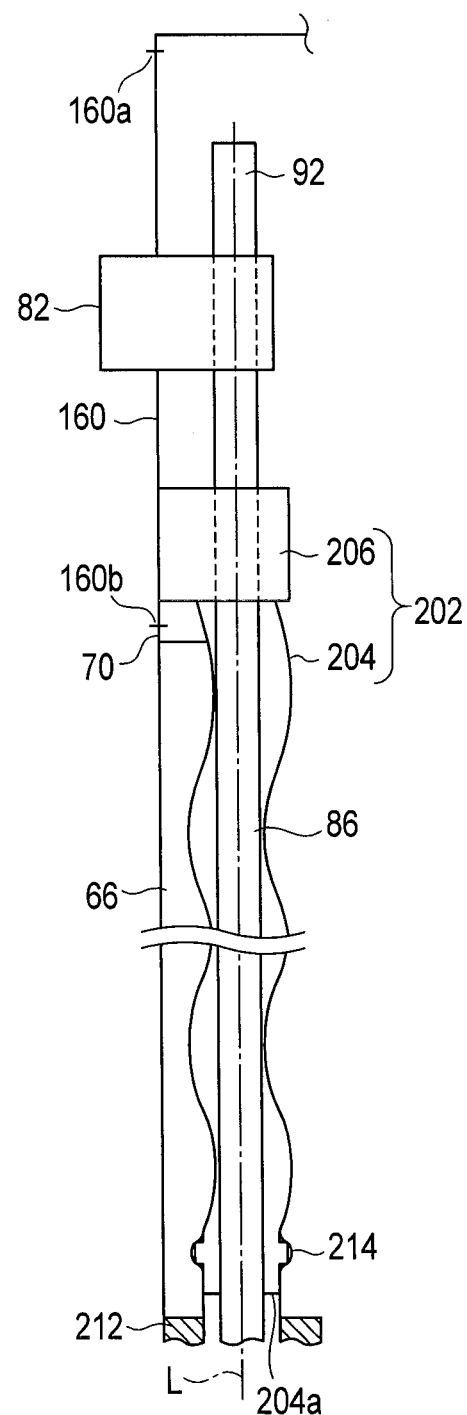
F I G. 11C

DRIVING FORCE TRANSMISSION MECHANISM FOR MEDICAL DEVICES

CROSS-REFERENCE TO RELATED APPLICATIONS

This application is a Continuation Application of PCT Application No. PCT/JP2016/059914, filed Mar. 28, 2016 and based upon and claiming the benefit of priority from prior Japanese Patent Application No. 2015-141233, filed Jul. 15, 2015, the entire contents of all of which are incorporated herein by reference.

BACKGROUND OF THE INVENTION

1. Field of the Invention

The present invention relates to a driving force transmission mechanism for medical devices.

2. Description of the Related Art

For example, in a specification of U.S. Patent Application Publication No. 2014/330079 is disclosed a driving force transmission mechanism for medical devices which can transmit driving force of a motor which is a driving source (an input section) arranged at a proximal end of an operation section as rotational driving force of a gear disposed at a distal end of a drive shaft having appropriate flexibility. The gear at the distal end of the drive shaft is arranged at a predetermined position in an insertion section for a body cavity or the like, and meshed with the other gear (an output section) in the driving force transmission mechanism. The driving force is transmitted from the motor to the drive shaft, the gear at the distal end of the drive shaft, and the other gear in the mentioned order, and rotation of the other gear enables a spiral tube attached to an outer circumference of the insertion section of the driving force transmission mechanism to rotate in a desired direction around a central axis of the insertion section.

BRIEF SUMMARY OF THE INVENTION

According to an aspect of the invention, there is provided a driving force transmission mechanism for medical devices, includes: a gear train to which rotational driving force is transmitted from a driving source, and which includes an output end from which the rotational driving force is output; a drive shaft including a support portion to which the rotational driving force is transmitted in a state where it is supported at the output end of the gear train; and a tubular portion including: an opening edge portion which allows the support portion of the drive shaft to be supported at the output end in a state where at least a part of the output end is accommodated in the tubular portion; and a first adjustment section which is configured to fix the gear train in a state where the drive shaft is inserted into the tubular portion and a distal portion of the drive shaft is arranged at a predetermined position where a driven portion is able to be driven and a state where a position of the output end of the gear train is adjusted relative to a position of the support portion of the drive shaft.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 4A is a schematic view showing a state where the operation section of the endoscope of the medical system according to the first embodiment is seen from a direction of an arrow IV in FIG. 2;

FIG. 4B is a schematic view showing a state where the operation section of the endoscope of the medical system according to the first embodiment is seen from the direction of the arrow IV in FIG. 2, and also showing a state where a protection hood and a case main body of an exterior case are removed from the state shown in FIG. 4A;

FIG. 10A is a schematic view showing a position at which the drive shaft of the driving unit is supported by the input section to the endoscope of the medical system according to the first embodiment, and a state where the fixed portion of the channel is fixed to the rigid tube while a distal end of a tube main body of the channel is fixed and the tube main body has a natural length;

FIG. 11B is a schematic view showing the position at which the drive shaft of the driving unit is supported by the input section to the endoscope of the medical system according to the first embodiment, and a state where the fixed portion of the channel is fixed to the rigid tube while the distal end of the tube main body of the channel formed longer than the tube main body of the channel shown in FIG. 10A is fixed and the tube main body is pushed in from the natural length state;

FIG. 11C is a schematic view showing the position at which the drive shaft of the driving unit is supported by the input section to the endoscope of the medical system according to the first embodiment, and a state where the fixed portion of the channel is fixed to the rigid tube while the distal end of the tube main body of the channel which is formed longer than the tube main body of the channel shown in FIG. 10A is fixed and the tube main body is further pushed in relative to the condition shown in FIG. 11B from the natural length state;

DETAILED DESCRIPTION OF THE INVENTION

A mode for embodying the present invention will now be described hereinafter with reference to the drawings.

First Embodiment

A first embodiment will be described with reference to FIG. 1 to FIG. 11C.

Figure 1:
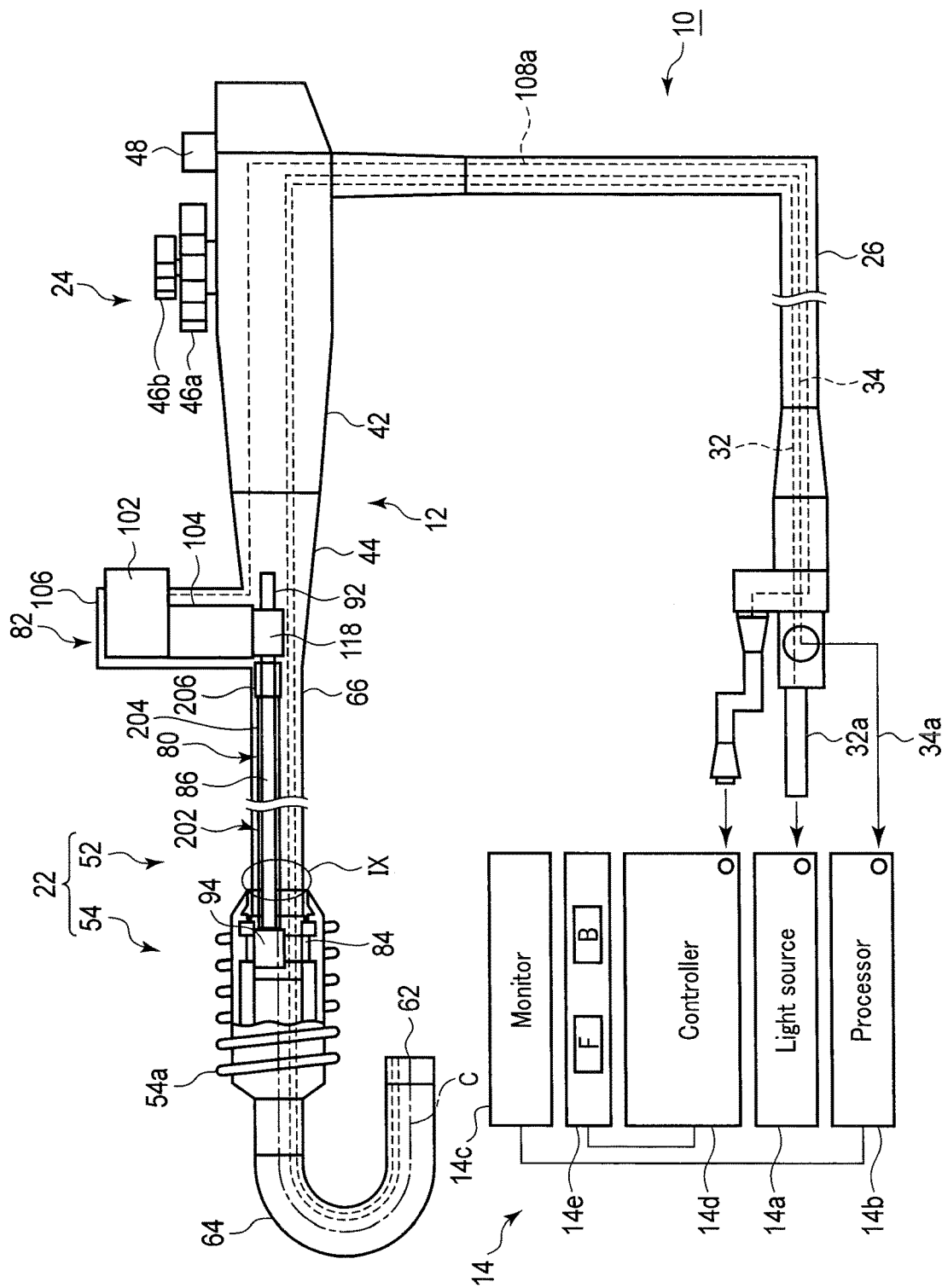
FIG. 1 is a schematic view showing a medical system according to first and second embodiments.

As shown in FIG. 1, a medical system 10 according to this embodiment includes an endoscope (a driving force transmission mechanism for medical devices) 12 which is inserted into a lumen of a living body, and a control system 14 formed of units connected to the endoscope 12. Here, the endoscope 12 will be described as the driving force transmission mechanism for medical devices, but it is also preferable to use a catheter or any other appropriate device as the driving force transmission mechanism for medical devices.

The control system 14 includes a light source unit 14a which emits illumination light to illuminate an observation target as a later-described illumination optical system 32, a processor (an image processing unit) 14b which processes an image captured by an imaging section of a later-described observation optical system 32, a monitor (a display section) 14c which displays a captured image, a controller 14d which controls the entire medical system 10, and an input unit 14e to input an instruction or the like to the controller 14d. As the input unit 14e, for example, a non-illustrated keyboard or foot switch is used. The foot switch as the input unit 14e includes a forward movement switch F and a backward movement switch B which control a later-described motor 102 and instruct to insert or remove a later-described insertion section 22 into or from a body cavity. As the controller 14d, it is possible to use not only a dedicated device but also a general-purpose processing device such as personal computer having an arbitrary program installed therein. Further, if an LED is used for the illumination light, it is possible to use the processor 14b as a power supply of not only the observation optical system 34 but also the illumination optical system 32. Alternatively, the light source 14a can be used as the power supply of the illumination optical system 32.

The endoscope 12 includes the insertion section 22, an operation section 24 provided on a proximal side of the insertion section 22, and a universal cable 26 extended from the operation section 24. The control system 14 is connected to the endoscope 12 through the universal cable 26 extended from the operation section 24. The illumination optical system 32 and the observation optical system 34 are inserted into the insertion section 22, the operation section 24 and the universal cable 26 of the endoscope 12, A light guide connector 32a of the illumination optical system 32 and a video signal cable 34a of the observation optical system 34 are inserted in the universal cable 26. Although a motor power supply cable 108a of a later-described driving unit 80 is inserted in the universal cable 26 in FIG. 1, it is also preferable to arrange it on an outer portion of the universal cable 26. The motor power supply cable 108a is connected to the controller 14d.

Figure 2:
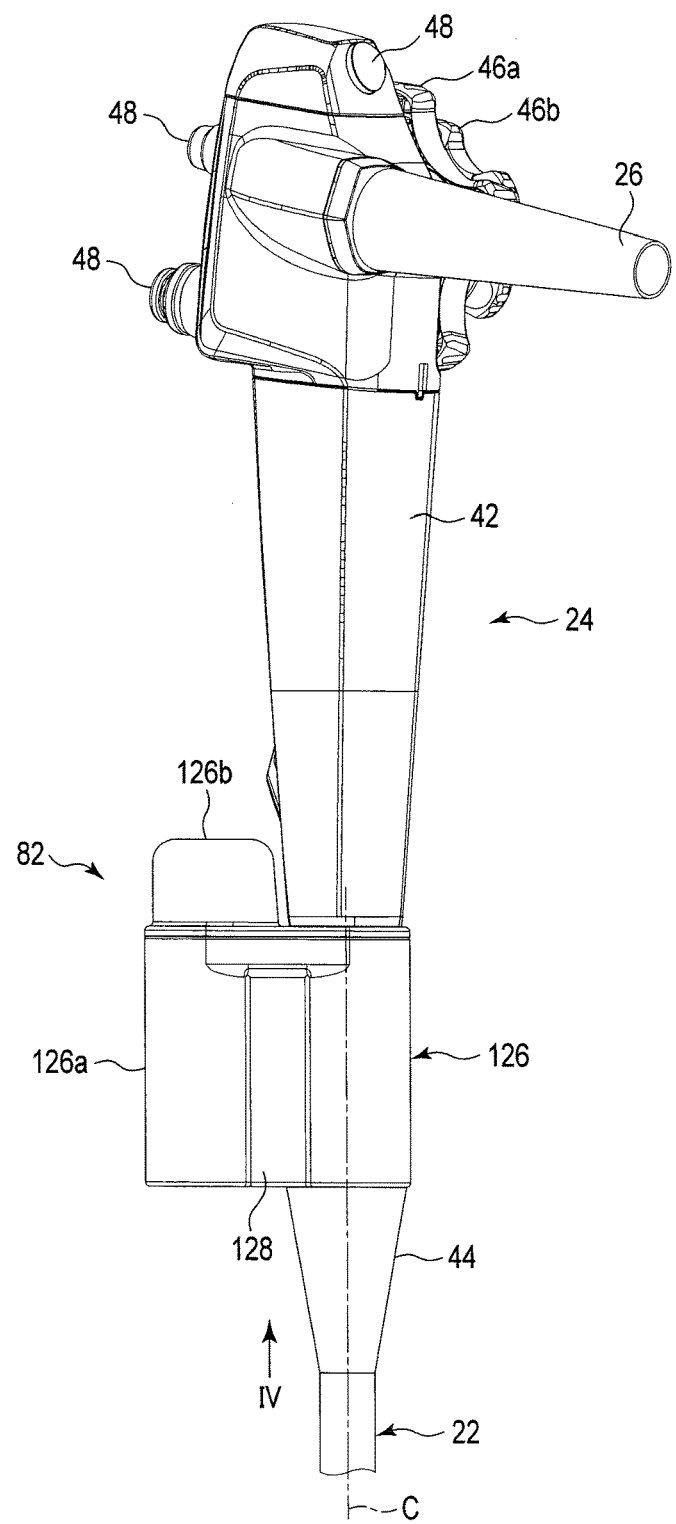
FIG. 2 is a perspective view showing a part of an endoscope of the medical system according to the first and second embodiments.

As shown in FIG. 2, the operation section 24 includes a grip section 42, a protection hood 44 which supports a proximal end of a later-described flexible tube 66 of the insertion section 22, and knobs 46a and 46b provided on the grip section 42, and a switch 48 which is provided on the grip section 42 and to which various kinds of instructions are assigned. The number of switch 48 is not restricted to one, and the multiple switches 48 may be provided. The switch 48 includes not only an electrical switch but also a mechanical switch such as a suction button and an air supply/water supply button. The protection hood 44 prevents the flexible tube 66 of the insertion section 22 from bending. The knob 46a can bend a later-described bending portion 64 of the insertion section 22 shown in FIG. 1 in an upward direction and downward direction by a rotation operation. The knob 46b can bend the bending portion 64 in a left direction and a right direction by a rotation operation. Although not shown, a proximal end opening of a treatment instrument insertion channel (a built-in component) is formed on a proximal side of the protection hood 44 of the operation section 24.

As shown in FIG. 1, the insertion section 22 includes an elongated insertion section main body 52 extended along a longitudinal direction, and a spiral tube 54. The insertion section main body 52 includes a distal rigid portion 62, the bending portion 64 provided on the proximal side of the distal rigid portion 62, and the flexible tube 66 provided on the proximal side of the bending portion 64. The flexible tube 66 has flexibility which follows bending of a pipeline in a body cavity or the like. The bending portion 64 is formed of a well-known structure. The bending portion 64 can bend in four directions, i.e., the upward direction, the downward direction, the left direction, and the right direction by operations of the knobs 46a and 46b in the operation section 24. A distal opening or the like of the non-illustrated treatment instrument insertion channel or the like through which a non-illustrated imaging section of the observation optical system 34, a cleaning nozzle, a forceps, or the like is inserted is provided in the distal rigid portion 62.

Figure 3:
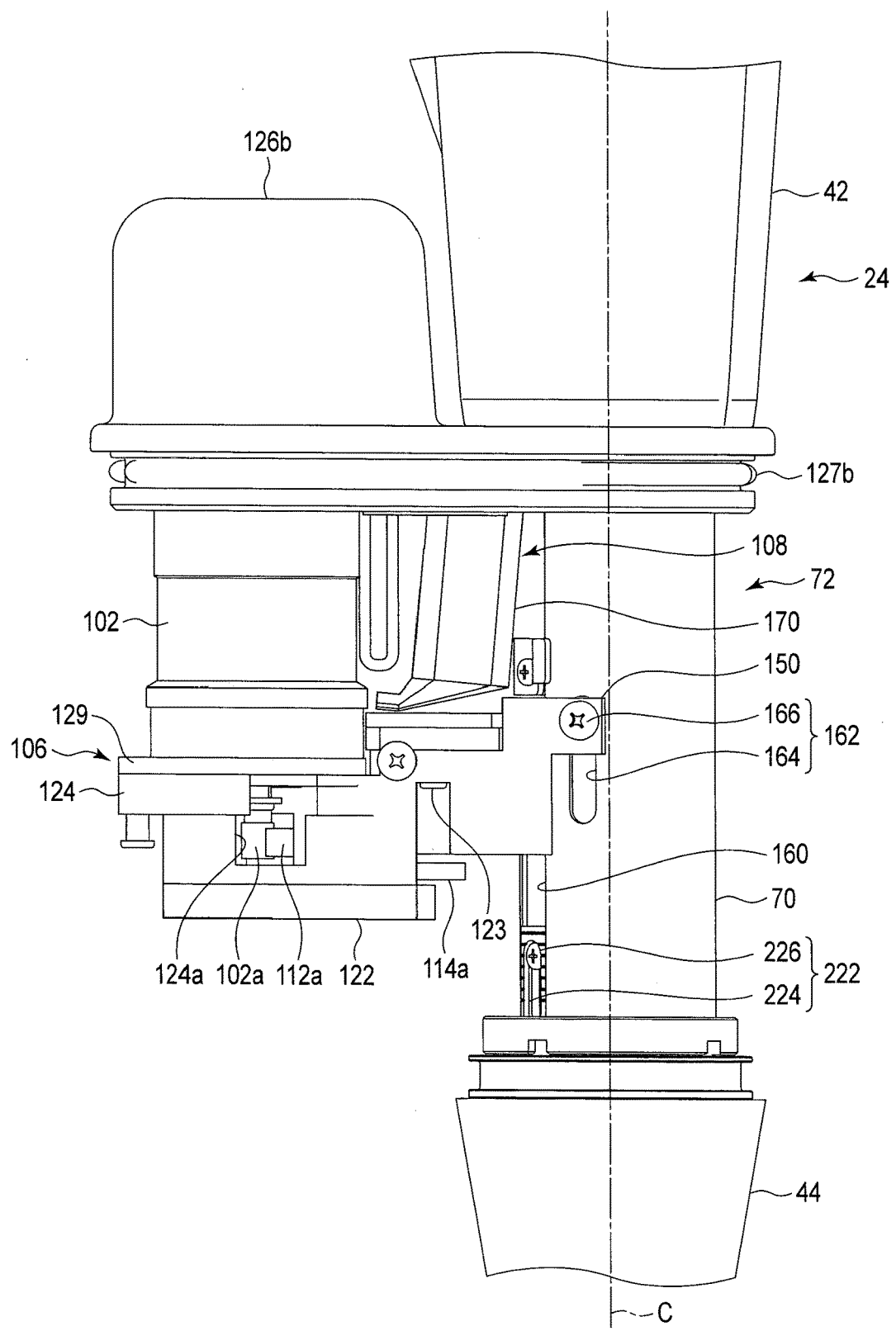
FIG. 3 is a schematic view showing a part of an inner structure of an operation section of the endoscope of the medical system according to the first embodiment.
Figure 4C:
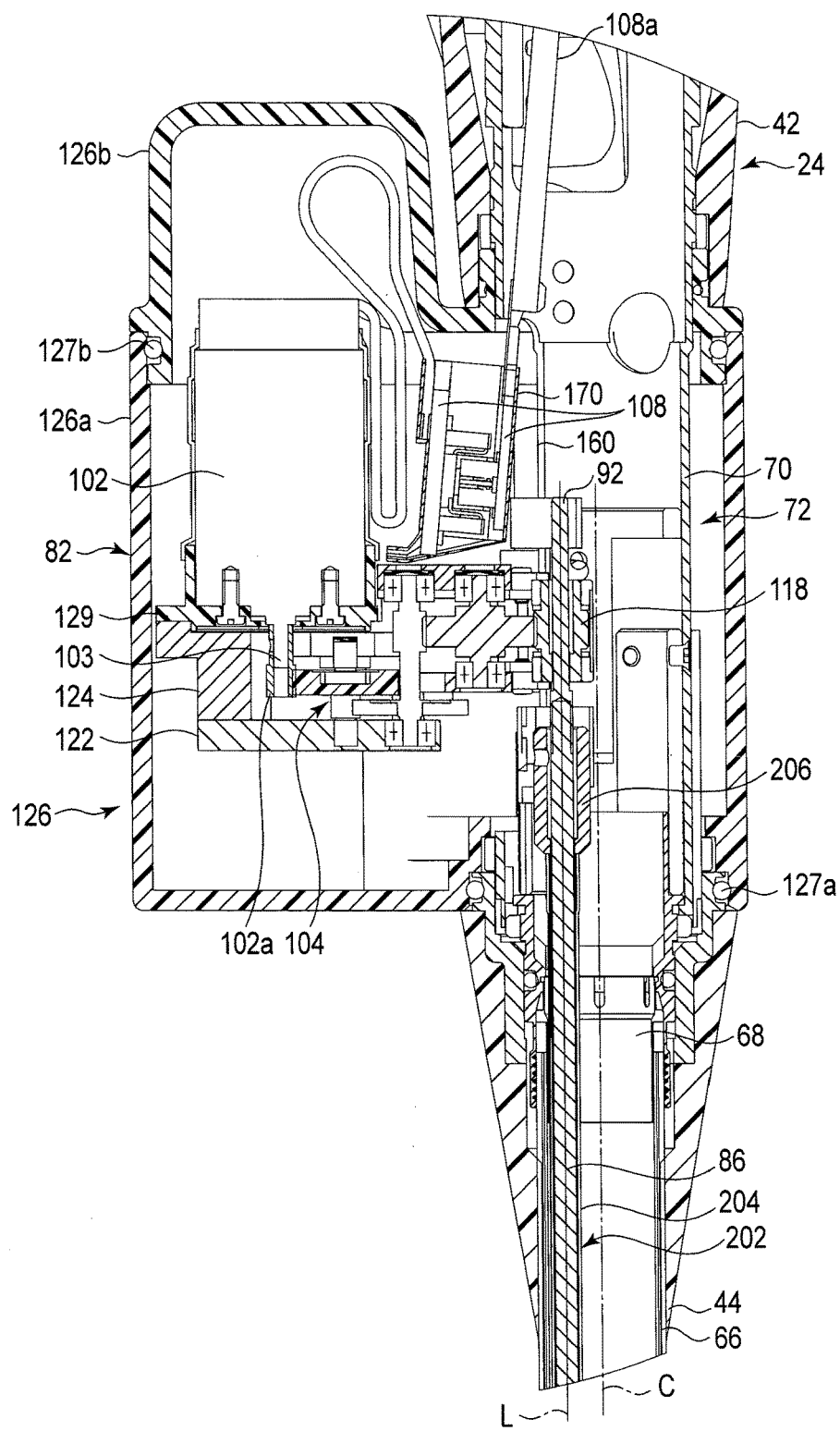
FIG. 4C is a schematic longitudinal cross-sectional view showing the inner structure of the operation section of the endoscope of the medical system according to the first embodiment taken along a line 4C-4C in FIG. 4A.
Figure 5A:
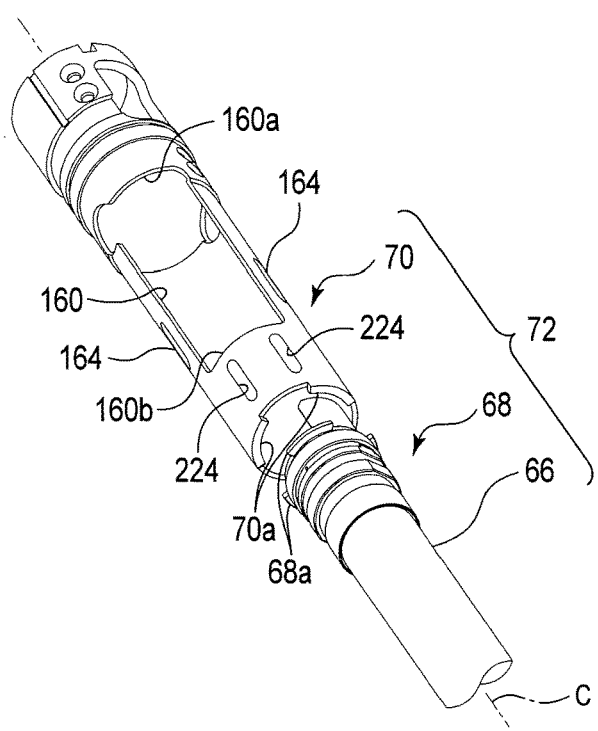
FIG. 5A is a schematic perspective view showing a rigid tube, a mouthpiece, and a proximal portion of a flexible tube arranged in the operation section of the endoscope of the medical system according to the first embodiment, and particularly showing a state where the mouthpiece is integrated with the proximal end of the flexible tube, and a state where the rigid tube is separated.
Figure 5B:
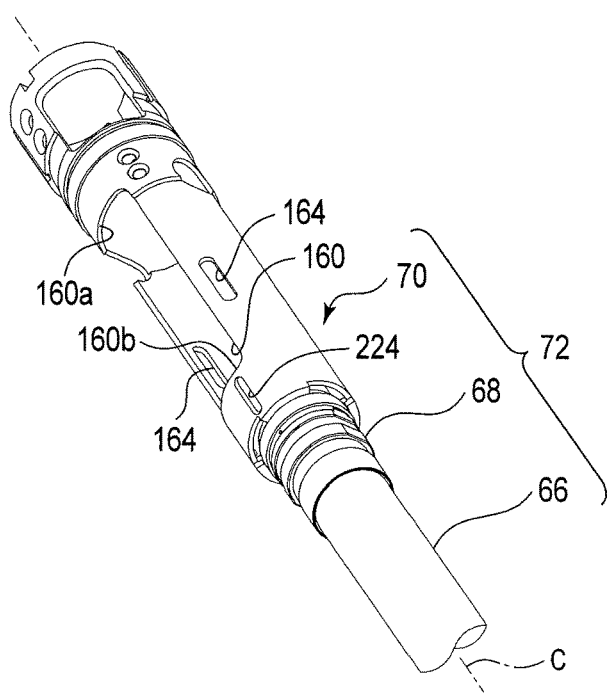
FIG. 5B is a schematic perspective view showing the rigid tube, the mouthpiece, and the proximal portion of the flexible tube arranged in the operation section of the endoscope of the medical system according to the first embodiment, and particularly showing a state where the mouthpiece is integrated with the proximal end of the flexible tube, and a state where the rigid tube is connected to the mouthpiece.

As shown in FIG. 3 to FIG. 4C, a rigid tube 70 coupled through a mouthpiece 68 coupled with a proximal end of the flexible tube 66 is arranged in the protection hood 44. As shown in FIG. 5A and FIG. 5B, the rigid tube 70, the mouthpiece 68, and the flexible tube 66 form a tubular portion 72. Further, a central axis C of the tubular portion 72 is defined by a distal portion and a proximal portion thereof.

The mouthpiece 68 is fixed to the proximal end of the flexible tube 66 shown in FIG. 5A. The mouthpiece 68 includes a flange 68a protruding outward in a radial direction. The rigid tube 70 includes a flange 70a protruding inward in the radial direction. The flange portions 68a and 70a are not annularly formed but discontinuously formed. Furthermore, when the flanges 68a and 70a are turned in a circumferential direction in a state where their central axes C are matched with each other, the flange 68a of the mouthpiece 68 can pass through the inner side of the flange 70a of the rigid tube 70. In this state, the rigid tube 70 and the mouthpiece 68 are relatively turned in a periaxial direction of the central axes C, thereby fixing the rigid tube 70 to the mouthpiece 68. Thus, as shown in FIG. 5B, the rigid tube 70 can be coupled with the mouthpiece 68 in a state depicted in FIG. 5A.

In this manner, the rigid tube 70 can be assembled from a rear end side of the flexible tube 66. Therefore, the rigid tube 70 does not have to be moved from the distal side toward the proximal side of the insertion section main body 52. That is, it is possible to save the effort of arranging the rigid tube 70 at the proximal end of the flexible tube 66 through the distal rigid portion 62, the bending portion 64, and the flexible tube 66. Thus, assembling properties at the time of disposing the rigid tube 70 to the proximal end of the flexible tube 66 can be greatly improved.

As shown in FIG. 1, the spiral tube 54 having a fin 54a spirally protruding on an outer periphery is disposed on an outer peripheral surface of the flexible tube 66 near, e.g., the distal portion thereof on the proximal side of the bending portion 64, so that it can be attached or detached from the distal side of the insertion section main body 52. The spiral tube 54 can be attached to or detached from a predetermined position on the flexible tube 66 through the distal rigid portion 62 and the bending portion 64 of the insertion section main body 52.

A driving unit 80 to drive the spiral tube 54 is provided in a region from the vicinity of a boundary between the insertion section 22 and the operation section 24 to, e.g., the distal portion of the flexible tube 66. The spiral tube 54 can rotate by driving force of the driving unit 80. Rotational directions of the spiral tube 54 are both periaxial directions of the central axis C of the insertion section main body 52. Moreover, the spiral tube 54 is used as an assist tool for insertion and removal to or from a pipeline, which assists insertion into a body cavity and also assists removal from an inserted state.

The driving unit 80 includes an input section 82 arranged near the boundary between the insertion section 22 and the operation section 24, an output section 84 arranged at, e.g., the distal portion of the flexible tube 66, and a drive shaft (a driving force transmitting section) 86 arranged between the input section 82 and the output portion 84.

Figure 6:
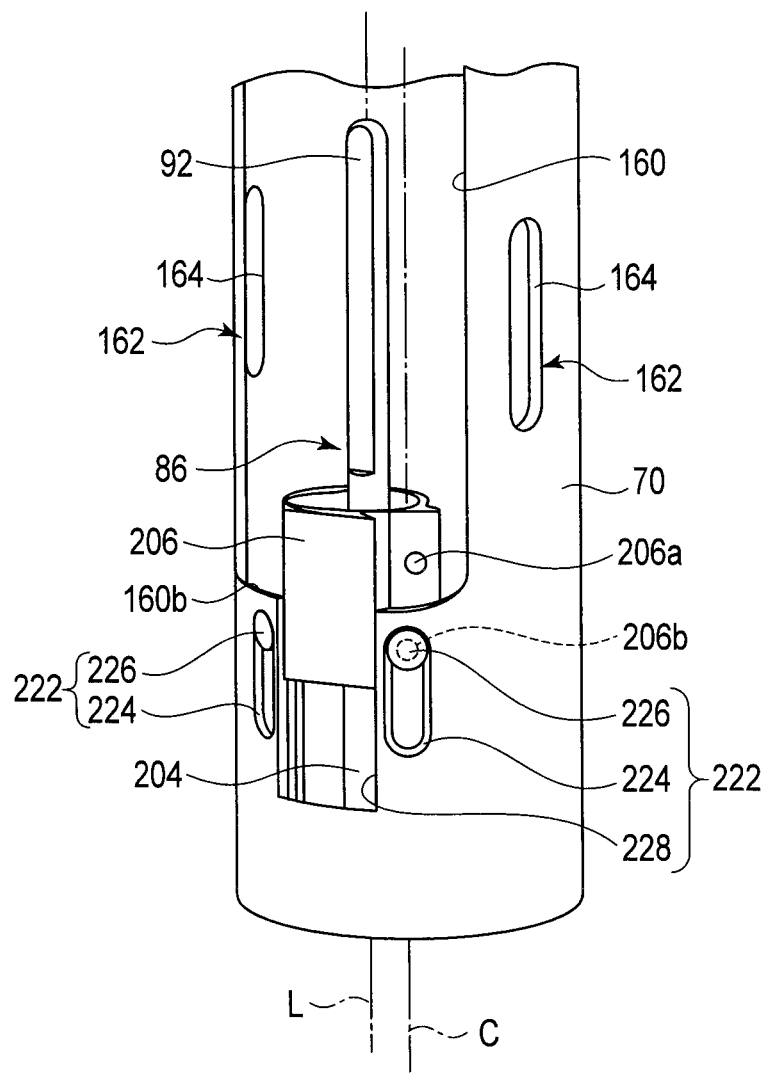
FIG. 6 is a schematic perspective view showing a state where a support portion of a drive shaft and a fixed portion of a channel can be accessed through an opening region of the rigid tube arranged in the operation section of the endoscope of the medical system according to the first embodiment.

As shown in FIG. 1 and FIG. 4C, the drive shaft 86 includes, at its proximal portion, a support portion 92 which is formed long to a later-described output end 118 of the input section 82, and is supported by the output end 118. As shown in FIG. 6, the support portion 92 is formed to have, e.g., a D-shaped lateral cross section. A distal side of the drive shaft 86 apart from the support portion 92 has appropriate firmness and flexibility. A gear 94 is fixed at a distal end of the drive shaft 86. The flexible tube 66 of the insertion section main body 52 includes the output section 84 as a ring which is rotatable in the periaxial direction of the central axis C. The output section 84 is formed as a gear which rotates in the periaxial direction of the central axis C by rotation of the gear 94.

Figure 7:
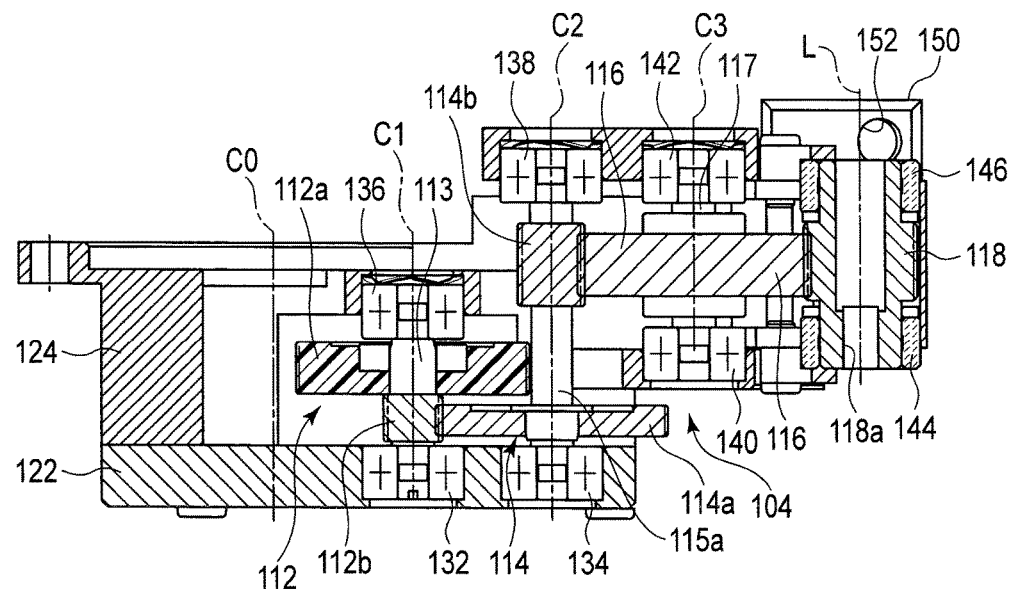
FIG. 7 is a schematic longitudinal cross-sectional view showing a state where a motor is eliminated from an input section of a driving unit connected to the rigid tube arranged in the operation section of the endoscope of the medical system according to the first embodiment taken along a line VII-VII shown in FIG. 8C.

As shown in FIG. 1, FIG. 3, and FIG. 4C, the input section 82 includes the motor (the driving source) 102, a gear train 104, a gearbox (a gear support frame) 106, and a substrate 108. The input section 82 is accommodated in the gear box 106 in a state where it protrudes in a direction orthogonal to a longitudinal direction of the insertion section 22 from the vicinity of the boundary between the insertion section 22 and the operation section 24. It is to be noted that, as shown in FIG. 7, it is preferable for the gear train 104 to include gears, e.g., four gear assemblies 112, 114, 116, and 118 to which rotational driving force is transmitted from the motor (the driving source) 102 in this example. The output end 118 can output the rotational driving force when driving force is transmitted thereto from the motor (the driving source) 102. In particular, when a gear ratio of the gears in the gear train 104 is adjusted, a rotational speed of a driving shaft 103 of the motor 102 can be output from the output end 118 with appropriate torque and an appropriate speed.

It is to be noted that the rotational driving force may be directly transmitted to the output end 118 from the driving shaft 103 of the motor 102 without using the gear assemblies 112, 114, and 116 in the gear trains 104 depending on selection of the motor 102 or a control method of the motor 102.

Figure 8A:
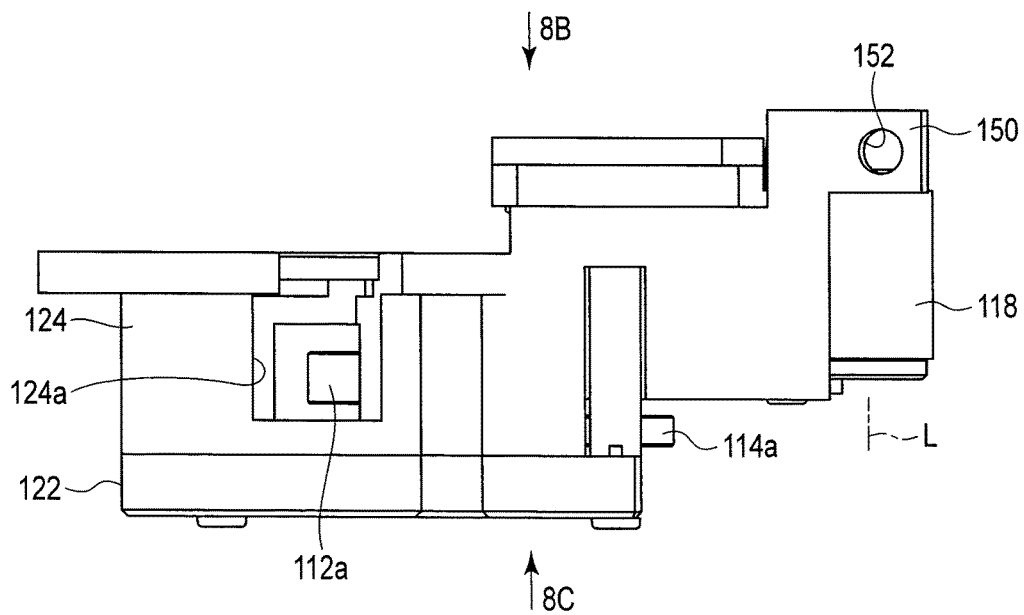
FIG. 8A is a schematic front view showing a gear box of the input section of the driving unit connected to the rigid tube arranged in the operation section of the endoscope of the medical system according to the first embodiment.
Figure 8B:
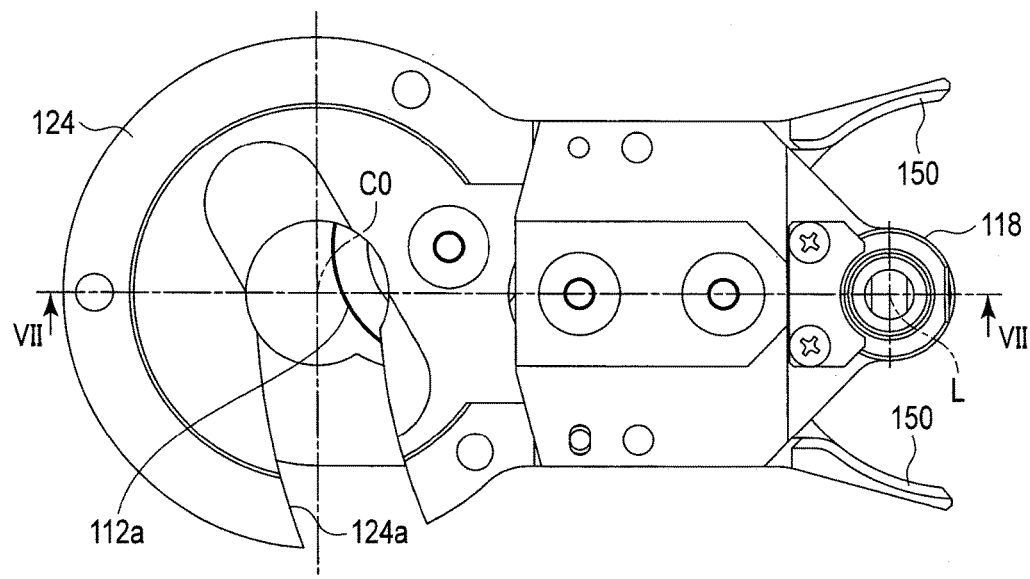
FIG. 8B is a schematic top view showing a state where the gear box of the input section of the driving unit connected to the rigid tube arranged in the operation section of the endoscope of the medical system according to the first embodiment is seen from a direction indicated by an arrow 8B in FIG. 8A.
Figure 8C:
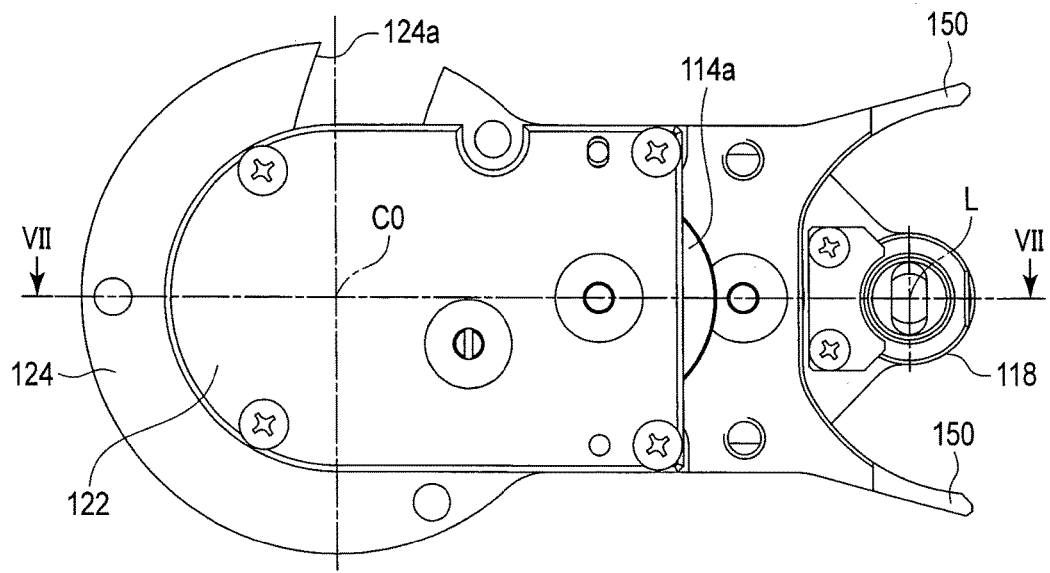
FIG. 8C is a schematic bottom view showing a state where the gear box of the input section of the driving unit connected to the rigid tube arranged in the operation section of the endoscope of the medical system according to the first embodiment is seen from a direction indicated by an arrow 8C in FIG. 8A.

As shown in FIG. 7 to FIG. 8C, the gear box 106 includes a base plate 122, a support body 124, and an exterior case 126. The base plate 122 and the support body 124 are fixed by a screw 123. The base plate 122 and the support body 124 support the motor 102 and the gear assemblies 112, 114, 116, and 118 in cooperation with each other. As will be described later, the support body 124 is fixed to the rigid tube 70. The first gear assembly 112 includes a large gear 112a and a small gear 112b. The second gear assembly 114 includes a large gear 114a and a small gear 114b.

A notch 124a is formed in the support body 124. At the time of fixing the motor 102 to the support body 124 through the notch 124a, the driving shaft 103 of the motor 102 can be passed through the notch 124a. Thus, in case of disposing the motor 102, the motor 102 can be disposed to the support body 124 from a direction orthogonal to the central axis C of the tubular portion 72. Therefore, after the operation section 24 is disposed to the proximal portion of the insertion section main body 52, the motor 102 can be easily arranged on the support body 124. It is preferable for a central axis C0 of the driving shaft 103 of the motor 102 to be fixed in a state where it is arranged parallel to a later-described central axis C1 as possible by a later-described insulating plate 129.

A gear 102a disposed to the driving shaft 103 of the motor 102 is meshed with the large gear 112a of the first gear assembly 112 in the gear train 104. The first gear assembly 112 is supported by both the base plate 122 and the support body 124. The large gear 114a of the second gear assembly 114 in the gear train 104 is meshed with the small gear 112b which rotates together with the large gear 112a of the first gear assembly 112. The second gear assembly 114 is supported by both the base plate 122 and the support body 124. The third gear assembly 116 in the gear train 104 is meshed with the small gear 114b which rotates together with the large gear 114a of the second gear assembly 114. The third gear assembly 116 is supported by the support body 124. The tubular output end 118 as the fourth gear assembly in the gear train 104 is meshed with the third gear assembly 116. The output end 118 is supported by the support body 124. It is to be noted that the large gear 112a of the first gear assembly 112 is made of, e.g., a rigid resin material or the like having electrical insulating properties. As shown in FIG. 4C, the motor 102 is supported by the support body 124 through the insulating plate 129 having the electrical insulating properties. Thus, the motor 102 and the endoscope 12 are electrically insulated. Moreover, GND of the observation optical system 34 in the endoscope 12 is electrically insulated and separated from GND of the motor 102.

One end (a lower end) of a rotary shaft 113 of the first gear assembly 112 and one end (a lower end) of a rotary shaft 115 of the second gear assembly 114 shown in FIG. 7 are supported by ball bearings 132 and 134 whose outer rings are fitted in a spigot joint to the base plate 122. Thus, the central axis C1 of the rotary shaft 113 of the first gear assembly 112 is parallel to a central axis C2 of the rotary shaft 115 of the second gear assembly 114. Therefore, it is possible to assure an accuracy of a central distance between the first gear assembly 112 and the second gear assembly 114.

The other end (an upper end) of the rotary shaft 113 of the first gear assembly 112 and the other end (an upper end) of the rotary shaft 115 of the second gear assembly 114 are supported by ball bearings 136 and 138 to the support body 124. One end (a lower end) and the other end (an upper end) of a rotary shaft 117 of the third gear assembly 116 are supported by ball bearings 140 and 142 to the support body 124. One end (a lower end) and the other end (an upper end) of the output end 118 are supported by slide bearings 144 and 146 made of a ceramic material to the support body 124. These slide bearings 144 and 146 can be miniaturized to the ball bearings. Using the slide bearings 144 and 146 made of the ceramic material enables preventing seizing of sliding surfaces of the slide bearings 144 and 146 themselves.

Since the central axes C1 and C2 maintain a state where they are parallel to each other, it is difficult for a central axis C3 of the rotary shaft 117 of the third gear assembly 116 to which the rotational driving force is transmitted from the second gear assembly 114 to deviate from a state the central axis C3 is parallel to the central axes C1 and C2, due to accuracies of the central axes C1 and C2. Since the central axes C1, C2, and C3 maintain the mutually-parallel state with the appropriate accuracies, it is difficult for a longitudinal axis L of the output end 118 as the fourth gear assembly to deviate from a state the longitudinal axis L is parallel to the central axes C1, C2 and C3. Thus, the rotational driving force of the driving shaft 103 of the motor 102 can be stably transmitted to the output end 118.

The support body 124 includes arms 150 fixed to the rigid tube 70 at a position which is distal to a position at which the motor 102 is supported. To further stably fix the arms 150 to the rigid tube 70, providing multiple, e.g., a pair of arms 150 is preferable, but providing one arm 150 can suffice depending on fixing force (a fixed state). It is to be noted that forming each arm 150 into a shape parallel to an outer peripheral surface of the rigid tube 70 is preferable. A screw hole 152 is formed in each arm 150.

As shown in FIG. 5A and FIG. 5B, the rigid tube 70 includes an opening edge portion 160 in a side surface. As shown in FIG. 4C, the output end 118 in the gear train 104 can be arranged in the rigid tube 70 through the opening edge portion 160 in the side surface of the rigid tube 70. In a state where at least a part of the output end 18 is placed in the opening region 160 of the rigid tube 70, the support portion 92 of the drive shaft 86 is supported by the output end 118. The opening edge portion 160 has, in a circumferential direction of the rigid tube 70, an opening width which enables arranging the output end 118 of the gear train 104 in the rigid tube 70. Further, the opening edge portion 160 has, along a longitudinal direction of the rigid tube 70, an opening length which enables appropriately moving the output end 118 of the gear train 104. A distance between an upper end (one end) 160a and a lower end (the other end) 160b of the opening edge portion 160 is set to be larger than the opening width. It is preferable to set a distance between the upper end 160a and the lower end 160b of the opening edge portion 160 to be approximately several times as large as a height of the output end 118 in the gear train 104 in particular. Furthermore, accessing the inside of the rigid tube 70 through this opening edge portion 160 enables appropriately adjusting arrangement or the like of built-in components.

As shown in FIG. 7, a fitting portion 118a is formed at the tubular output end 118 in the gear train 104. The fitting portion 118a is formed near the lower end of the output end 118 in particular. The fitting portion 118a is formed into a D-like shape. As described above, the drive shaft 86 includes, for example, the support portion 92 having a cross section formed into, e.g., a D-like shape at a proximal end of the drive shaft 86. Therefore, as shown in FIG. 4C, the support portion 92 can be fitted in the fitting portion 118a. Thus, in a state where the support portion 92 of the drive shaft 86 is supported by the output end 118 of the gear train 104, the rotational driving force from the motor (the driving source) 102 is transmitted to the gear 94 at the distal portion from the support portion 92 at the proximal portion of the drive shaft 86.

A difference in length caused due to a variation in manufacture, an influence of temperatures or humidity, and others can be produced in the drive shaft 86. There is a possibility that the flexible tube 66 is appropriately bent. Thus, as regards the variation in manufacture or bending of the flexible tube 66, the support portion 92 could be formed to have a length which enables maintaining a fitted state of the fitting portion 118a and the support portion 92. It is preferable for the length of the support portion 92 to be approximately several times as large as the length of the output end 118. As will be described later, the support portion 92 can move to the output end 118 along the axial direction. It is to be noted that accommodating the support portion 92 of the drive shaft 86 between the upper end and the lower end of the rigid tube 70 both in a state where the flexible tube 66 is straight and a state where the flexible tube 66 is appropriately bent.

As shown in FIG. 6, the support portion 92 of the drive shaft 86 is placed at a position which is able to be accessed through the opening edge portion 160 of the rigid tube 70 in a state where the output section 84 at the distal portion of the drive shaft 86 is arranged at a predetermined position where the spiral tube 54 can be driven. It is to be noted that movement of the output section 84 shown in FIG. 1 toward the proximal side is regulated by forming the output section 84 into an appropriate shape for a later-described rigid base 212.

Here, as shown in FIG. 3 and FIG. 6, the rigid tube 70 includes a first adjustment section (a gear train fixing section) 162. The first adjustment section 162 can fix the gear train 104 in a state where the gear 94 at the distal portion of the drive shaft 86 is arranged in the output section 84 corresponding to a predetermined position where the spiral tube 54 of the flexible tube 66 can be driven and a state where a position of the output end 118 in the gear train 104 is adjusted to the position of the support portion 92 of the drive shaft 86 along the longitudinal axis L.

The first adjustment section 162 includes elongated holes 164 which are long and extend along the axial direction of the central axis C, which are near the opening edge portion 160 along the circumferential direction of the central axis C of the opening edge portion 160 of the rigid tube 70 and which are shorter than the opening length of the opening edge portion 160, and fixing bodies (screws) 166 which pierce through the elongated holes 164. Like the arms 150 of the support body 124, to further stably fix the arms 150 to the rigid tube 70, it is preferable to provide multiple, e.g., a pair of the elongated holes 164, but providing one elongated hole 164 can suffice depending on fixing force (a fixed state).

As shown in FIG. 3, the arms 150 of the support body 124 are arranged outside the outer peripheral surface of the rigid tube 70. The elongated holes 164 of the first adjustment section 162 and the screw holes 152 of the arms 150 shown in FIG. 7 and FIG. 8A can be matched with each other, respectively in a radial direction orthogonal to the axial direction of the central axis C. In this state, the arms 150 and the rigid tube 70 can be fixed by the fixing bodies 166 of the first adjustment section 162. At this time, positions of the arms 150 to the rigid tube 70 can be adjusted by determining positions in the elongated holes 164 of the first adjustment section 162 at which the fixing bodies 166 are fixed along the axial direction of the central axis C. In this manner, the pair of arms 150 are fixed in a state where the rigid tube 70 is held. Thus, determining a position at which the pair of arms 150 are fixed to the first adjustment section 162 along the axial direction of the central axis C enables adjusting the position of the output end 118 to an appropriate position in the axial direction of the central axis C relative to the rigid tube 70.

As shown in FIG. 4, the substrate 108 connected to the motor 102 is arranged on, e.g., an upper side of the gear box 106. The substrate 108 is arranged between the motor 102 and the rigid tube 70. As shown in FIG. 3, the substrate 108 is covered with a heat shrinkable tube 170. The heat shrinkable tube 170 can make a region which electrically connects the substrate 108 with the motor 108 into a drip-proof type.

As shown in FIG. 4A to FIG. 4C, the exterior case 126 which covers the outer side of the base plate 122 having the motor 102 disposed thereto and the support body 124 includes a case main body 126a and a cap 126b which covers the upper side of the motor 102. The case main body 126a covers a greater part of the gear box 106. The case main body 126a covers the lower side of the gear box 106 in particular. An O-ring 127a is arranged between the case main body 126a and the protection hood 44. Thus, a liquid or the like can be prevented from entering the case main body 126a from the protection hood 44. An O-ring 127b is arranged between the case main body 126a and the cap 126b. Thus, a liquid or the like is prevented from entering the case main body 126a from a part between the case main body 126a and the cap 126b.

As shown in FIG. 4A, when the operation section 24 side is seen from the insertion section 22 side, the case main body 126a is formed into an annular shape like an athletics track field formed of two long sides and two semicircles. When the O-ring 127b is arranged in an inner region of edge portions of the exterior case 126, there is a fear that the long sides of the edge portions of the exterior case 126 are expanded by elasticity of the O-ring 127b. In this case, there is a possibility that water-tightness of the gear box 106 is not assured. Here, to assure the water-tightness of the gear box 106, concave portions 128 which are recessed toward the inner side are formed in the long sides of the case main body 126a of the exterior case 126, respectively. In this case, a person skilled in the arm can easily understand that the edge portions of the exterior case 126 are hardly deformed in an opening direction when the concave portions 128 are present as compared with a case where the concave portions 128 are not formed in the case main body 126a. Thus, forming the concave portions 128 enables easily assuring the water-tightness provided by the O-ring 127b.

Here, as shown in FIG. 1, FIG. 4C, FIG. 6, and FIG. 9, a channel 202 is arranged on the outer side of the drive shaft 86. The channel 202 includes a tube main body 204 into which the drive shaft 86 is inserted and which protects the outer side of the drive shaft 86 over substantially the entire length, and a fixed portion 206 which is fixed to the proximal end of the tube main body 204 and also fixed to the rigid tube 70. The drive shaft 86 is inserted into not only the tube main body 204 but also the fixed portion 206. The tube main body 204 is made of a resin material having flexibility with the electrical insulating properties and abrasion resisting properties.

The flexible tube 66 includes the rigid base 212. The base 212 supports the output section 84 which rotates in a periaxial direction of the central axis C on the basis of rotation of the gear 94 at the distal portion of the drive shaft 86 by rotation of the drive shaft 86. The gear 94 of the drive shaft 86 meshed with the output section 84 shown in FIG. 1 is supported by the base 212 of the flexible tube 66 at a predetermined position of the flexible tube 66 in a state where movement toward the proximal side is regulated. It is to be noted that the gear 94 of the drive shaft 86 is supported to be rotatable in the periaxial direction of the longitudinal axis L parallel to the central axis C.

Figure 9:
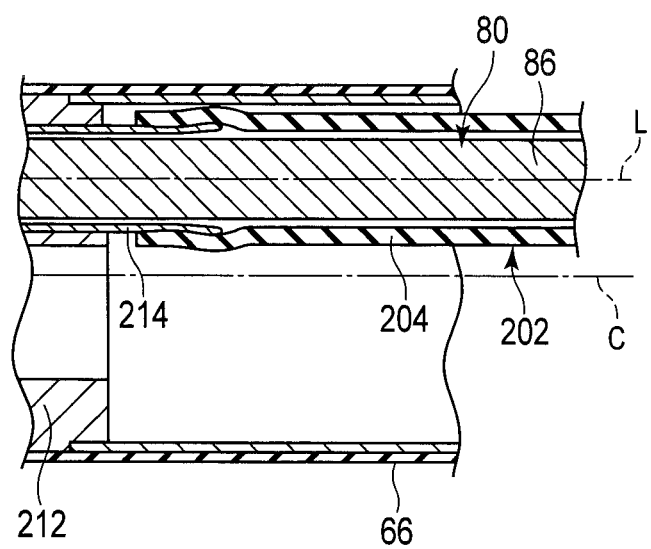
FIG. 9 is a schematic longitudinal cross-sectional view showing a position of an insertion section of the endoscope of the medical system according to the first embodiment indicated by reference sign IX in FIG. 1 in an enlarging manner.

As shown in FIG. 9, a tubular mouthpiece 214 protruding toward the proximal side in the longitudinal axis L is formed in the base 212. A distal end 204a of the later-described tube main body 204 of the channel 202 is fixed to the mouthpiece 214. Thus, one end 204a of the channel 202 is fixed to the base 212. The other end of the channel 202 is extended to the vicinity of the opening edge portion 160 of the rigid tube 70 through the flexible tube 66.

As shown in FIG. 6, the rigid tube 70 includes a second adjustment section 222 which can fix the fixed portion 206 of the channel 202. The second adjustment section 222 of the rigid tube 70 is provided on the distal side of the first adjustment section 162 of the rigid tube 70 along the longitudinal direction of the rigid tube 70. In a state where a position of the fixed portion 206 of the channel 202 is adjusted relative to the rigid tube 70, the second adjustment section 222 can fix the fixed portion 206 of the channel 202. At this time, the drive shaft 86 protected by the tube main body 204 is inserted into the tube main body 204 of the channel 202 and, on the other hand, the gear 94 at the distal portion of the drive shaft 86 is arranged at a predetermined position where the output section 84 and the spiral tube 54 can be driven.

The fixed portion 206 includes screw holes 206a and 206b which are apart from each other along the axial direction of the central axis C of the rigid tube 70. The second adjustment section 222 includes elongated holes 224 which are shorter than the opening length of the opening edge portion 160 and which are long and extend along the axial direction of the central axis C, in the vicinity of the lower end 160b of the opening edge portion 160 of the rigid tube 70, and fixing bodies (screws) 226 which pierce through the elongated holes 224. To further stably fix the fixed portion 206 to the rigid tube 70, providing multiple, e.g., a pair of elongated holes 224 is preferable, but providing one elongated hole 224 can suffice depending on fixing force (a fixed state). Further, the second adjustment section 222 fixes one of the screw holes 206a and 206b of the fixed portion 206 by using the fixing body (the screw) 226 through the elongated hole 224 of the rigid tube 70.

As shown in FIG. 6, the fixed portion 206 of the channel 202 is arranged on the inner side of the outer peripheral surface of the rigid tube 70. The elongated hole 224 of the second adjustment section 222 can be matched with one of the screw holes 206a and 206b of the fixed portion 206 in the radial direction orthogonal to the axial direction of the central axis C. In this state, the fixed portion 206 and the rigid tube 70 can be fixed by each fixing body 226 of the second adjustment section 222. At this time, a position of the fixed portion 206 to the rigid tube 70 can be adjusted by determining a position in each elongated hole 224 of the second adjustment section 222 at which the fixing body 226 is fixed along the axial direction of the central axis C. Thus, the position of the fixed portion 206 of the channel 202 to the rigid tube 70 can be adjusted to an appropriate position in the axial direction of the central axis C by determining a position at which the fixed portion 206 of the channel 202 is fixed relative to the second adjustment section 222 along the axial direction of the central axis C. Selecting one of the screw holes 206a and 206b of the fixed portion 206 likewise enables adjusting a position of the fixed portion 206 to the second adjustment section 222 of the rigid tube 70.

It is preferable that the second adjustment section 222 includes rails 228 which suppress movement of the fixed portion 206 in the circumferential direction. Thus, at the time of the moving the fixed portion 206 to the rigid tube 70 along the longitudinal direction, a displacement in the circumferential direction of the central axis C can be avoided, and movement in a desired direction can be facilitated.

Next, functions of the medical system. 10 according to this embodiment will now be described. An assembling order at the time of assembling the endoscope 12 will be roughly described herein in particular.

As shown in FIG. 5A and FIG. 5B, the rigid tube 70 is appropriately fitted to the mouthpiece 68 at the proximal end of the flexible tube 66. Thus, in case of fixing the rigid tube 70 to the mouthpiece 68 at the proximal end of the flexible tube 66, the rigid tube 70 does not have to be fitted on the outer side of the distal rigid portion 62, the bending portion 64, and the flexible tube 66 of the insertion section main body 52.

At this time, the illumination optical system 32, the observation optical system 34, a non-illustrated curving wire between the bending portion 64 and the knobs 46a and 46b, and a built-in component such as a motor power supply cable 108a connected to the substrate 108 of the motor 102 are also inserted into the tubular portion 72 including the rigid tube 70. It is to be noted that, as shown in FIG. 1, the illumination optical system 32, the observation optical system 34, the built-in component, e.g., the motor power supply cable 108a of the motor 2 are appropriately connected to the control system 14 through the universal cable 26 when the endoscope 12 is used.

Several working procedures to arrange the drive shaft 86 in the tubular portion 72 in a state where the drive shaft 86 is inserted into the channel 202 can be considered. For example, the drive shaft 86 having the gear 94 disposed at the distal end in a state where the distal end 204a of the tube main body 204 of the channel 202 is fixed to the mouthpiece 214 of the base 212 can be inserted into the tube main body 204 and the fixed portion 206 of the channel 202. In this case, the drive shaft 86 is inserted from the distal end 204a toward the proximal end of the tube main body 204 of the channel 202. Further, after the drive shaft 86 is appropriately inserted in the tube main body 204 and the fixed portion 206 of the channel 202, the gear 94 may be arranged at a predetermined position where it is meshed with the output section 84 of the base 212, and the distal end 204a of the tube main body 204 of the channel 202 may be fixed to the base 212. In case of fixing the distal end 204a of the tube main body 204 of the channel 202 to the base 212, combining fitting with bonding is preferable. It is to be noted that, since the channel 202 is fixed to the mouthpiece 214 of the base 212, it does not rotate even though the drive shaft 86 rotates.

Figure 10B:
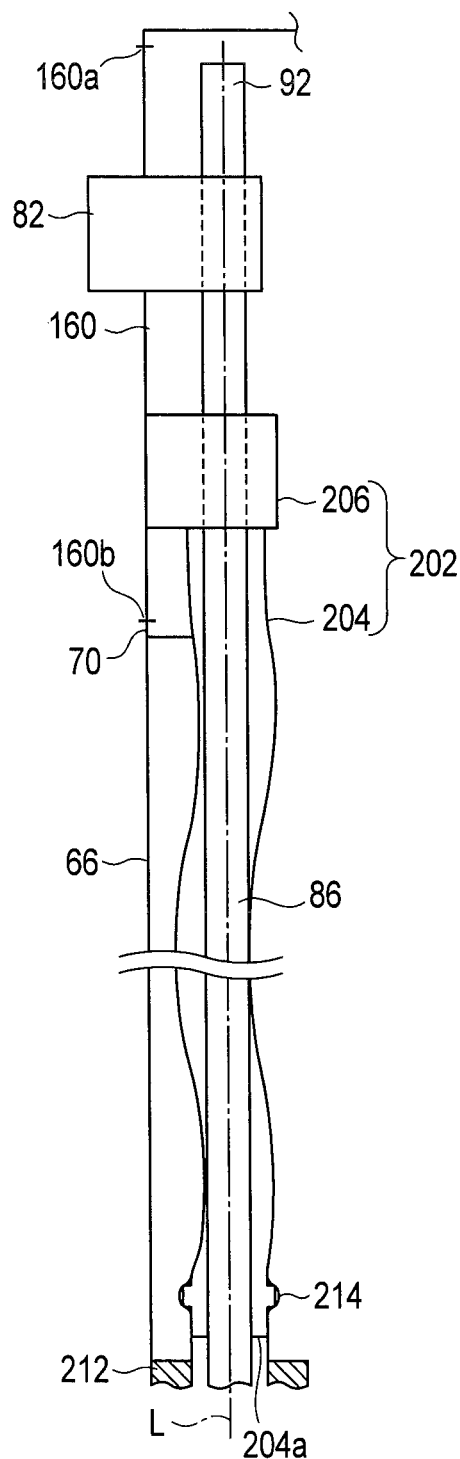
FIG. 10B is a schematic view showing the position at which the drive shaft of the driving unit is supported by the input section to the endoscope of the medical system according to the first embodiment, and a state where the fixed portion of the channel is fixed to the rigid tube while the distal end of the tube main body of the channel is fixed and the tube main body is pushed in from the natural length state.
Figure 10C:
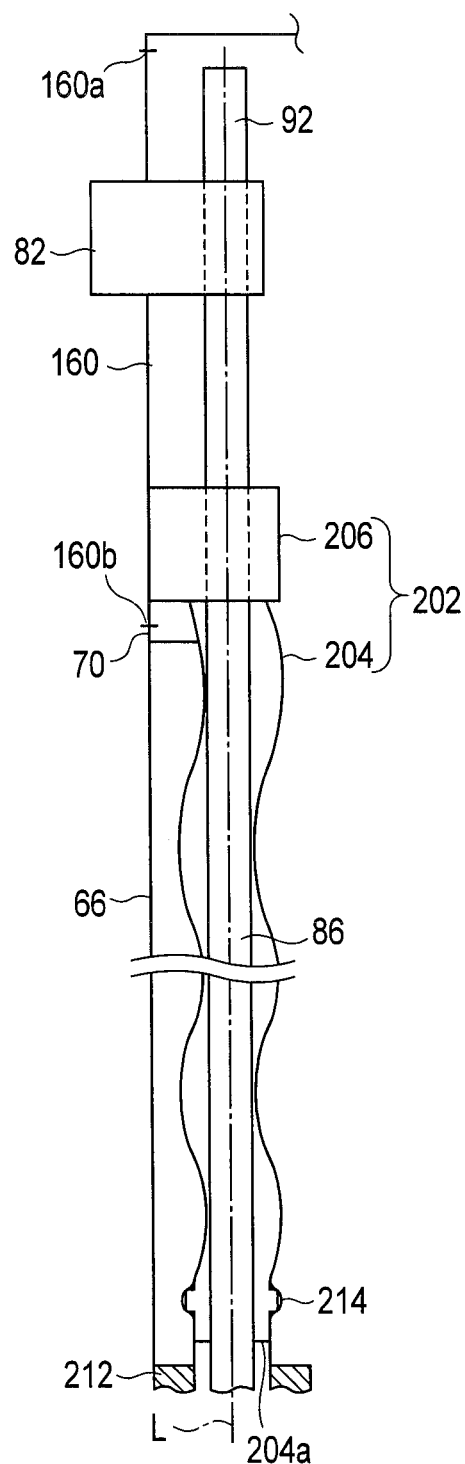
FIG. 10C is a schematic view showing the position at which the drive shaft of the driving unit is supported by the input section to the endoscope of the medical system according to the first embodiment, and a state where the fixed portion of the channel is fixed to the rigid tube while the distal end of the tube main body of the channel is fixed and the tube main body is further pushed in relative to a condition shown in FIG. 10B from the natural length state.

The fixed portion 206 at the proximal portion of the channel 202 is fixed to the second adjustment section 222 of the rigid tube 70 after adjusting a length of the tube main body 204. At this time, as shown in FIG. 10A, when the fixed portion 206 is fixed to the rigid tube 70 in a state where the tube main body 204 has a natural length, there is a possibility that the inner peripheral surface of the tube main body 204 is caused to abut on the outer peripheral surface of the drive shaft 86 for a long distance along the longitudinal direction due to bending of the flexible tube 66. On the other hand, as shown in FIG. 10C, when the tube main body 204 is extremely shortened from the natural length state, positions at which the inner peripheral surface of the tube main body 204 abuts on the outer peripheral surface of the drive shaft 86 can be increased even though the flexible tube 66 is straight. As shown in FIG. 10B, when the fixed portion 206 is fixed to an appropriate position relative to the rigid tube 70, a distance for which the inner peripheral surface of the tube main body 204 abuts on the outer peripheral surface of the drive shaft 86 due to bending of the flexible tube can be adjusted, and the positions at which the inner peripheral surface of the tube main body 204 abuts on the outer peripheral surface of the drive shaft 86 can be reduced when the flexible tube 66 is straight. Thus, when the drive shaft 86 is rotated, an abutting area between the outer peripheral surface of the drive shaft 86 and the inner peripheral surface of the tube main body 204 is adjusted to be reduced as much as possible.

For example, it is preferable that the fixed portion 206 is fixed to the rigid tube 70 in a state where the distal end 204a of the tube main body 204 is fixed to the mouthpiece 214 of the base 212, and where the tube main body 204 is pushed in for approximately 2 mm to 3 mm from the natural length.

Here, as shown in FIG. 6, the second adjustment section 222 of the rigid tube 70 includes the elongated holes 224. The fixed portion 206 includes the two screw holes 206a and 206b. Thus, the one screw hole 206a of the fixed portion 206 and the elongated hole 224 of the rigid tube 70 may be fixed by the fixing body 226, and the other screw hole 206b of the fixed portion 206 and the elongated hole 224 of the rigid tube 70 may be fixed by the fixed body 226 screw. Since the screw holes 206a and 206b of the fixed portion 206 shown in FIG. 6 are appropriately selected so that a state shown in FIG. 10B can be provided. Thus, since the fixed portion 206 includes the two screw holes 206a and 206b, a width of an adjustment enabled range in case of fixing the fixed portion 206 to the second adjustment section 222 of the rigid tube 70 can be made larger than that when only one screw hole is provided.

When the gear 94 at the distal end of the drive shaft 86 is arranged at an appropriate position where the output section 84 and the spiral tube 54 can be driven, the support portion 92 at the proximal portion of the drive shaft 86 is present at a position where it can be accessed from the outer side through the opening edge portion 160 of the rigid tube 70. At this time, the support portion 92 at the proximal portion of the drive shaft 86 protrudes toward the proximal side beyond the fixed portion 206 of the channel 202.

Further, the output end 118 of the gear train 104 is fitted to the support portion 92 of the drive shaft 86 from the proximal side. At this time, the support portion 92 protrudes toward the proximal side from the output end 118 along the longitudinal axis L.

The longitudinal axis L of the drive shaft 86 is provided at a position deviating outward in the radial direction from the central axis C of the flexible tube 66. Thus, when the flexible tube 66 is bent, the support portion 92 moves from the output end 118 along the axial direction of the longitudinal axis L. That is, the support portion 92 moves from the output end 118 along the axial direction of the longitudinal axis L on the basis of a bending direction and a bending level of the flexible tube 66. The support portion 92 and the output end 118 can maintain a state where a load cannot be applied in the axial direction of the longitudinal axis depending on their fitting position. In particular, the fitting portion 118a is formed near the lower end of the output end 118. Thus, the length of the support portion 92 could be set so that a fitted state between the fitting portion 118a and the support portion 92 can be maintained. That is, even if the upper end of the support portion 92 is pulled in to the upper end of the outer end 118 due to bending or the like of the flexible tube 66, maintaining the fitted state between the fitted portion 118a and the support portion 92 can suffice. Thus, a position of the fitted portion 118a of the output end 118 of the gear box 106 to the support portion 92 of the drive shaft 86 is adjusted, and the arms 150 of the gear train 104 are temporarily fixed to the elongated holes 164 by using the fixed bodies (the screws) 166.

After confirming that the support portion 92 can appropriately move relative to the output end 118 by proper bending of the flexible tube 66, as shown in FIG. 3, the arms 150 of the gear box 106 are firmly fixed to the elongated holes 164 by using the fixing bodies (the screws) 166. In this manner, the gear train 104 is fixed to the first adjustment section 162 of the rigid tube 70. That is, on the basis of the position of the support portion 92 of the drive shaft 86 to the rigid tube 70, the input section 82 is fixed to the rigid tube 70 in a state where the position of the output end 118 shown in FIG. 4 is adjusted.

At this time, the central axis C1 of the rotary shaft 113 of the first gear assembly 112 (112a, 112b) of the gear train 104 and the central axis C2 of the rotary shaft 115 of the second gear assembly 114 (114a, 114b) are maintained at an equal distance by the ball bearings 132 and 134 shown in FIG. 7. Furthermore, the central axes C1 and C2 of the gear train 104 are parallel or substantially parallel to the central axis C of the tubular portion 72. Moreover, the central axis C3 of the third gear assembly 116 and the longitudinal axis L of the output end 118 are likewise parallel or substantially parallel to the central axis C of the tubular portion 72 shown in FIG. 3.

Additionally, the motor 102 is disposed at a predetermined position to the support body 124 of the gear box 106 through the notch 124a. That is, the motor 102 is moved from a direction to get away from the central axis C of the tubular portion 72 in the endoscope 12 toward a direction to get closer to the same, thereby supporting the motor 102 by the support body 125. At this time, the central axis C0 of the driving shaft 103 of the motor 102 is also supported in a state where it is parallel or substantially parallel to the central axis C of the tubular portion 72.

As shown in FIG. 4C, the case main body 126a of the exterior case 126 is arranged on the protection hood 44 through the O-ring 127a. Further, the cap 126b of the exterior case 126 is put on the base plate 122 and the support body 124. The case main body 126a of the exterior case 126 suppresses outward expansion of the O-ring 127b by using its concave portion 128 (see FIG. 4A). Thus, the watertightness of the gear box 106 can be achieved by the O-ring 127b.

After such an operation, the endoscope 12 is appropriately performed by a proper operation.

In case of using the endoscope 12, as shown in FIG. 1, the universal cable 26 of the endoscope 12 is appropriately connected to the control system 14. The spiral tube 54 is arranged at an appropriate position of the insertion section main body 52 in an appropriate direction through the distal rigid portion 62 and the bending portion 64 of the insertion section main body 52. In a state where the spiral tube 54 is disposed to the insertion section main body 52, the central axis of the spiral tube 54 is substantially coaxial with the central axis C of the tubular portion 72.

The support portion 92 (see FIG. 4C) of the drive shaft 86 is locked and fitted in the output end 118 to be movable along the longitudinal axis L to the fitting portion 118a (see FIG. 7) of the output end 118 of the gear train 118. Thus, rotation of the driving shaft 103 of the motor 102 of the input section 82 can be transmitted to the drive shaft 86 through the gear train 104. That is, the rotational driving force input to the input section 82 is output to the output section 84 through the gear 94 at the distal end of the drive shaft 86.

When the forward movement switch F of the foot switch 14e shown in FIG. 1 is pressed, the rotational driving force input in the input section 82 is transmitted to the spiral tube 54 through the drive shaft 86 and the output section 84, and the spiral tube 54 rotates in an appropriate direction. The spiral tube (an assist tool) 54 rotates around the central axis C of the tubular portion 72 in particular. Furthermore, the distal end of the insertion section 22 is moved from an inlet of a body cavity toward an inner side by press force provided by the fin 54a. On the other hand, when the backward movement switch B of the foot switch 14e is pressed, the rotational driving force input in the input section 82 is transmitted to the spiral tube 54 through the drive shaft 86 and the output section 84, and the spiral tube 54 rotates in a direction opposite to the counterpart when the forward movement switch F is pressed. The distal end of the insertion section 22 is moved from the inner side toward the inlet of the body cavity by the press force provided by the fin 54a. Thus, this medical system 10 assists insertion of the insertion section 22 into, e.g., a body cavity, and also assists removal of the insertion section 22 from the body cavity.

At this time, the support portion 92 of the drive shaft 86 shown in FIG. 4C can move along the longitudinal axis L of the output end 118 of the gear train 104. When the drive shaft 86 is rotated by the rotational driving force of the input section 82 through the support portion 92 of the drive shaft 86, the drive shaft 86 is twisted. Thus, an entire length of the drive shaft 86 is shortened. At this time, the support portion 92 of the drive shaft 86 moves toward the distal side in the output end 118 of the gear train 104. However, the support portion 92 protrudes on the proximal side of the output end 118, even if the entire length of the drive shaft 86 is shortened by twisting, the fitted state of the support portion 92 and the fitting portion 118a of the output end 118 is maintained. Moreover, since the proximal end of the support portion 92 maintains a state that it protrudes on the proximal side beyond the fitting portion 118a of the output end 118 irrespective of a bent state and a straight state of the flexible tube 66, the fitted state of the support portion 92 and the fitting portion 118a of the output end 118 is maintained even though the entire length of the drive shaft 86 is shortened due to the twisting. Thus, in the endoscope 12 according to this embodiment, the positional adjustment of the input section 82 of the driving unit 80 to the support portion 92 of the drive shaft 86 enables excellently transmitting the driving force from the motor (the driving source) 102 to the distal end of the drive shaft 86 even if the length of the drive shaft 86 changes.

As described above, according to the medical system 10 of this embodiment, the following can be said.

The first adjustment section 162 of the rigid tube 70 of the tubular portion 72 can fix the gear train 104 to a position of the support portion 92 of the drive shaft 86 in a state where the drive shaft 86 is inserted into the tubular portion 72 and the gear 94 at the distal portion of the drive shaft 86 is arranged at a predetermined position which enables driving the output section 84 and the spiral tube 54 as a driven portion, and a state where a position of the output end 118 of the gear train 104 is adjusted relative to the position of the support portion 92 of the drive shaft 86. In this manner, in a state where the position of the gear train 104 is adjusted in accordance with the position of the support portion 92 to the rigid tube 70, the gear train 104 can be fixed to the rigid tube 70. Thus, even if the drive shafts 86 have different lengths, the driving force from the motor (driving source) 102 can be excellently transmitted to the distal end of each drive shaft 86 irrespective of a difference in length. Further, since a relative position of the output end 118 of the gear trains 104 can be moved relative to the support portion 92 of the drive shaft 92, it is possible to reduce the need for considering play when the flexible tube 66 of the insertion section main body 52 is bent.

The second adjustment section 222 of the rigid tube 70 of the tubular portion 72 can fix the fixed portion 206 of the channel 202 in a state where the drive shaft 86 protected by the channel 202 is inserted into the tubular portion 72 and the gear 94 at the distal portion of the drive shaft 86 is arranged at the predetermined position which enables driving the output section 84 and the spiral tube 54 as the driven portion, and in a state where the position of the fixed portion 206 of the channel 202 is adjusted. In this manner, the fixed portion 206 can be fixed to the rigid tube 70 in a state where the distal end 204a of the tube main body 204 of the channel 202 is fixed to the insertion section main body 52, and a state where the position of the fixed portion 206 to the rigid tube 70 is adjusted. Therefore, even if there is a difference in length between the tube main bodies 204 of the channels 202 in manufacture or the like, the fixed portion 206 can be fixed to the rigid tube 70 by adjusting play of the tube main body 204 of each channel 202 irrespective of the difference in length. Thus, appropriately controlling friction between the inner peripheral surface of the tube main body 204 and the outer peripheral surface of the drive shaft 86 enables excellently transmitting the driving force from the motor (the driving source) 102 to the distal end of the drive shaft 86.

Figure 11A:
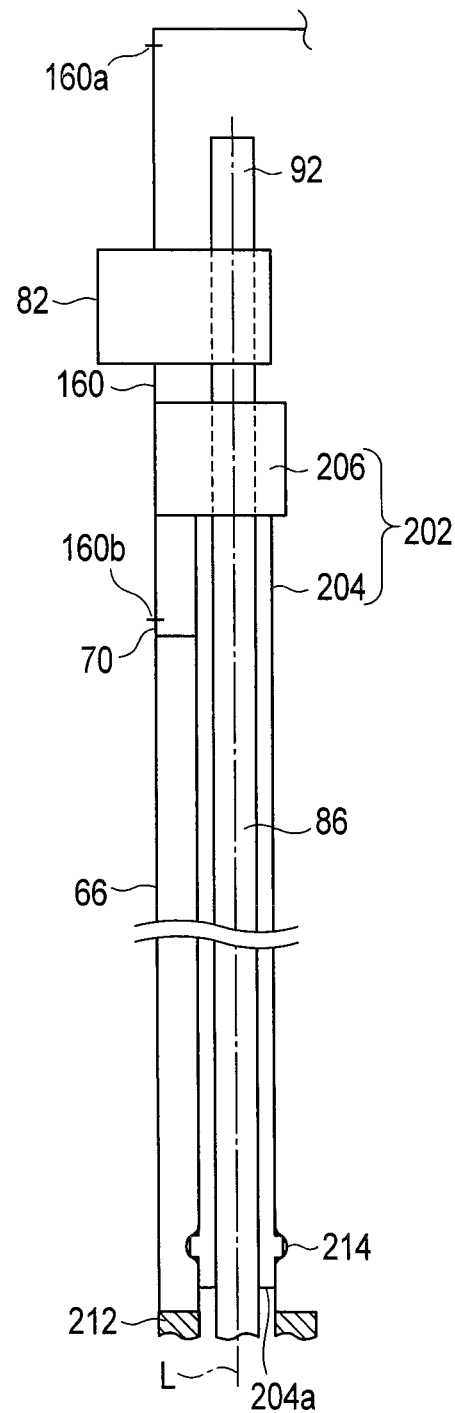
FIG. 11A is a schematic view showing the position at which the drive shaft of the driving unit is supported by the input section to the endoscope of the medical system according to the first embodiment, and a state where the fixed portion of the channel is fixed to the rigid tube while a distal end of a tube main body of a channel which is formed longer than the tube main body of the channel shown in FIG. 10A is fixed and the tube main body has the natural length.

In case of manufacturing tube main bodies 204, as shown in FIG. 10A and FIG. 11A, there is a possibility that lengths vary due to a manufacturing accuracy and others like a case of manufacturing the drive shafts 86. FIG. 10A and FIG. 11A show a difference in position between the fixed portions 206 on the basis of a difference in length between the tube main bodies 204 of the channels 202. The tube main body 204 of the channel 202 shown in FIG. 10A is formed longer than the tube main body 204 of the channel 202 shown in FIG. 11A. Thus, in a state where the distal end 204a of the tube main body 204 of the channel 202 is appropriately fixed to the mouthpiece 214 of the base 212, a position of the fixed portion 206 at the proximal end of the tube main body 204 to the opening edge portion 160 of the rigid tube 70 can vary depending on the tube main body 204 to be used.

As shown in FIG. 10C and FIG. 11C, when the fixed portion 206 of the channel 202 is fixed to the rigid tube 70 in a state where the tube main body 204 is pushed in too much relative to the natural length, friction is produced at multiple positions between the outer peripheral surface of the drive shaft 86 and the inner peripheral surface of the tube main body 204 due to rotation of the drive shaft 86, and there is a possibility that the friction extremely increases as a whole. On the other hand, as shown in FIG. 10A and FIG. 11A, when the fixed portion 206 of the channel 202 is fixed while the tube main body 204 has the natural length, the distal end 204a of the tube main body 204 of the channel 202 pulls the tube main body 204 to come off the mouthpiece 214 of the base 212 due to bending of the flexible tube 66. Even if a state where the distal end 204a of the tube main body 204 of the channel 202 is fixed to the mouthpiece 214 of the base 212 is maintained, there is fear that the outer peripheral surface of the drive shaft 86 abuts on the inner peripheral surface of the tube main body 204 for a relatively long distance. Thus, friction may be possibly produced between the outer peripheral surface of the drive shaft 86 and the inner peripheral surface of the tube main body 204 for a relatively long distance due to rotation of the drive shaft 86, and the friction may extremely increase as a whole. Thus, even if the fixed portion 206 of the channel 202 is fixed to the rigid tube 70 in the state where the tube main body 204 has the natural length or if it is fixed to the rigid tube 70 in the state where the tube main body 204 is pushed in too much relative to the natural length, there is fear that the friction extremely increases as a whole.

For example, as shown in FIG. 10B and FIG. 11B, it is preferable that the fixed portion 206 is fixed to the rigid tube 70 in a state where the distal end 204a of the tube main body 204 is fixed to the mouthpiece 214 of the base 212, and a state where the tube main body 204 is pushed in for approximately 2 mm to 3 mm from the natural length. In this case, frictional force can be reduced as compared with that in a state where the fixed portion 206 of the channel 202 is fixed to the rigid tube 70 when the tube main body 204 has the natural length, and the frictional force can be reduced as compared with that in a state where the tube main body 204 is pushed in too much relative to the natural length.

The fixed portion 206 arranged at the proximal end of the tube main body 204 includes the screw holes 206a and 206b which are apart from each other in the longitudinal direction. Thus, selecting one of the screw holes 206a and 206b in accordance with the length of the tube main body 204 enables appropriately adjusting looseness of the tube main body 204, then fixing the fixed body 226 to the second adjustment section 222, and fixing the fixed portion 206 to the rigid tube 70.

Second Embodiment

A second embodiment will now be described with reference to FIG. 12 to FIG. 14. This embodiment is a modification of the first embodiment, and like reference numerals denote the same members or members having the same functions as the members described in the first embodiment as much as possible to omit a detailed description thereof.

Figure 12:
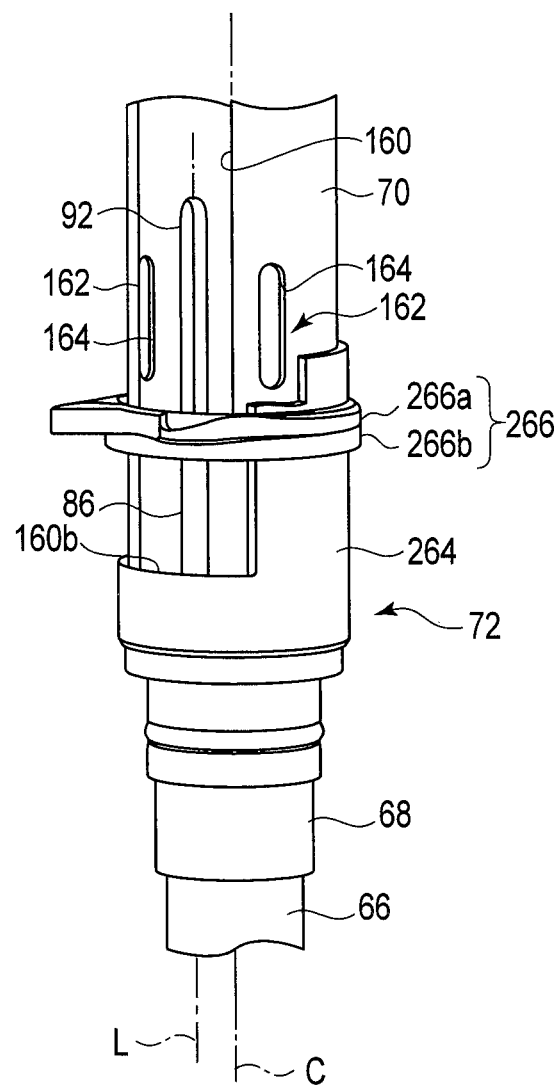
FIG. 12 is a schematic perspective view showing a state where a male screw portion is formed to the rigid tube arranged in the operation section of the endoscope of the medical system according to the second embodiment, double nuts are arranged on the male screw portion, and the support portion of the drive shaft can be accessed through the opening region.
Figure 13:
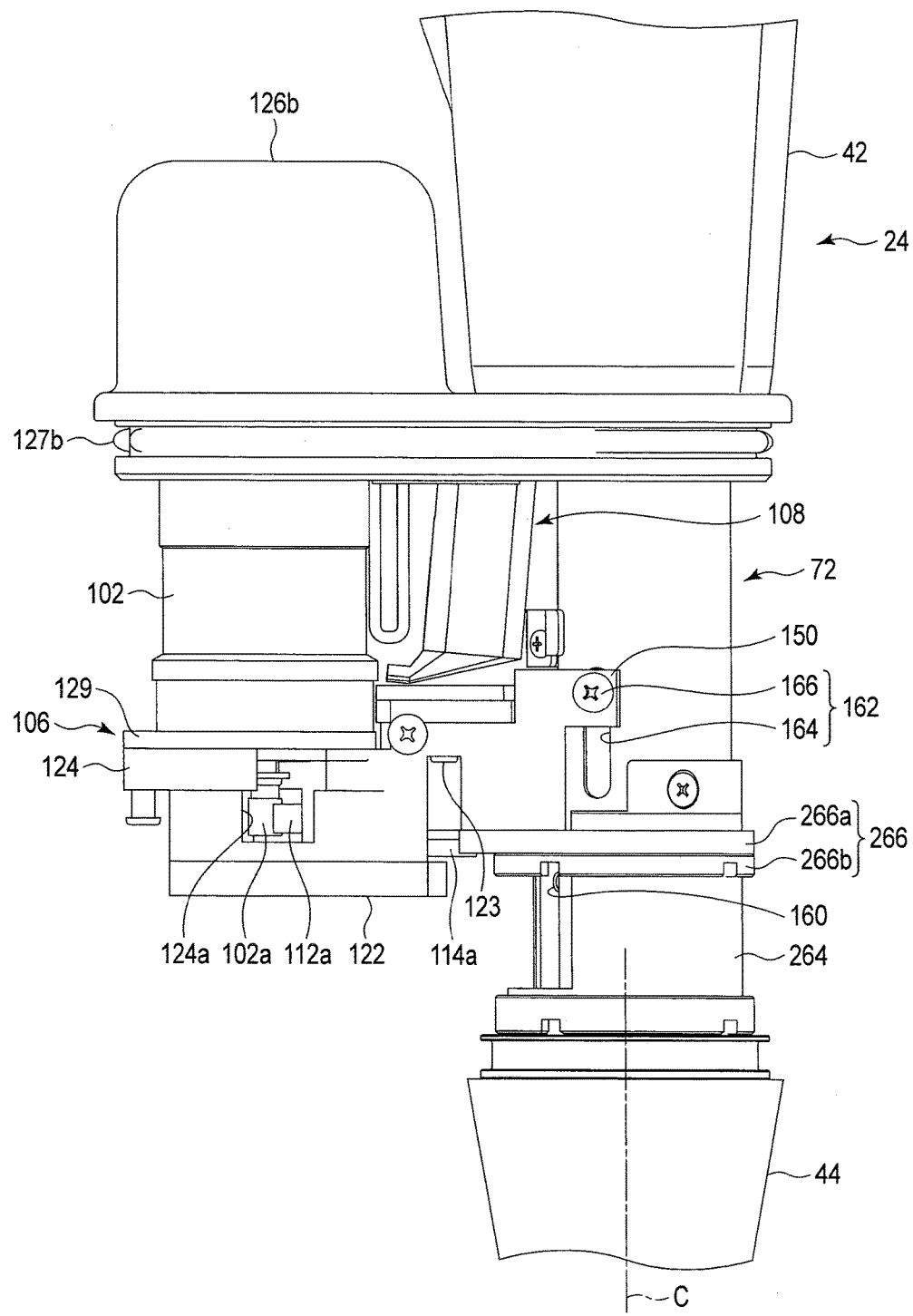
FIG. 13 is a schematic view showing a part of the inner structure of the operation section of the endoscope of the medical system according to the second embodiment.
Figure 14:
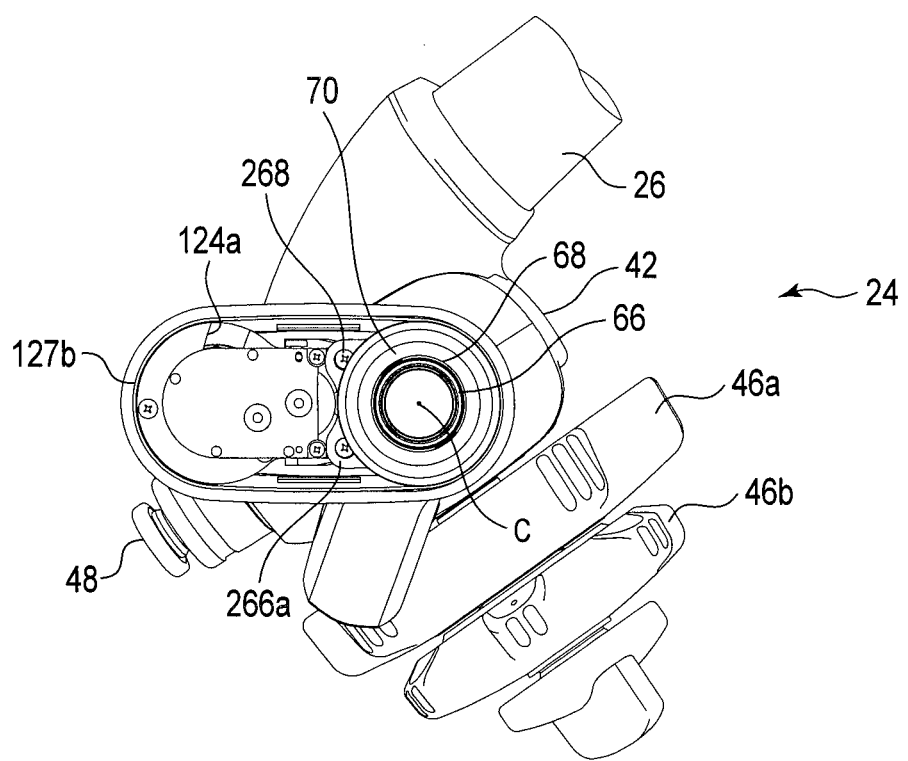
FIG. 14 is a schematic view showing a state where the protection hood is removed from the operation section of the endoscope of the medical system according to the second embodiment and the case main body of the exterior case is removed from the driving unit from a direction of an arrow IV in FIG. 2.

As shown in FIG. 12 and FIG. 13, the first adjustment section 162 includes a male screw portion 264 formed on an outer side of a rigid tube 70, and a nut 266 which can adjust a screwing position to the male screw portion 264 and supports a gear train 104 in a state where a position of an output end 118 of the gear train 104 is adjusted, in addition to the elongated hole 164.

It is preferable that the nut 266 of the first adjustment section 162 is double nuts. The nut 266 includes two nuts 266a and 266b. Further, the first adjustment section 162 fixes the gear box 106 to the nut 266a by using a fixing body (screw) 268 (see FIG. 14).

When the double nuts 266a and 266b are used, movement of the double nuts 266a and 266b to the male screw portion 264 can be suppressed. Using the double nuts 266a and 266b enables preventing rattling of the nut 266a to the rigid tube 70. Furthermore, the gear box 106 is fixed and supported from the lower side of the upper nut 266a by the fixing body (screw) 268. When the rattling of the nut 266a to the rigid tube 70 is prevented, it is possible to avoid rattling of the gear box 106 fixed to the nut 266 by the fixing body (screw) 268, i.e., the gear train 104.

Thus, the gear box 106 can be supported in a more stable fixed state together with the fixing body (screw) 166 arranged in the elongated hole 164.

Although not shown, it is preferable that the fixed portion 206 of the channel 202 is fixed to the rigid tube 70 in the same manner as that described in the first embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A driving force transmission mechanism for medical devices, comprising:
   a gear train to which rotational driving force is transmitted from a driving source, the gear train including-an output end from which the rotational driving force is output;
   a drive shaft including a support portion to which the rotational driving force is transmitted in a state where the drive shaft is supported at the output end of the gear train; and
   a tubular portion including:
      an opening edge portion which allows the support portion of the drive shaft to be supported at the output end in a state where at least a part of the output end is accommodated in the tubular portion;
      a first adjustment section configured to fix the gear train in a plurality of different positions, in a state where the drive shaft is inserted into the tubular portion and a distal portion of the drive shaft is arranged at a predetermined position where a driven portion is able to be driven and a state where a position of the output end of the gear train is adjusted relative to a position of the support portion of the drive shaft; and
      a flexible tube having flexibility into which the drive shaft is inserted, and in which a distal end portion of the drive shaft is arranged.

2. The mechanism according to claim 1, wherein the support portion of the drive shaft is locked in a periaxial direction of a longitudinal axis of the tubular portion and fitted to the output end of the gear train to be movable along the longitudinal direction of the tubular portion.

3. The mechanism according to claim 1, wherein:
   the tubular portion includes: a rigid tube including the first adjustment section,
   the flexible tube is arranged on a distal end side of the rigid tube, and
   the support portion of the drive shaft is movable along the longitudinal direction of the tubular portion in accordance with bending of the flexible tube.

4. The mechanism according to claim 1, wherein the first adjustment section is configured to move the output end of the gear train along the longitudinal direction of the tubular portion, and configured to fix the output end of the gear train at a position to which the output end has been moved along the longitudinal direction of the tubular portion.

5. The mechanism according to claim 4, wherein the first adjustment section includes an elongated hole which extends along the longitudinal direction of the tubular portion.

6. The mechanism according to claim 4, wherein the first adjustment section includes:
   a male screw portion formed on an outer side of the tubular portion; and
   a nut which is configured to adjust a screwing position to the male screw portion and supports the gear train in a state where a position of the output end of the gear train is adjusted.

7. The mechanism according to claim 1, comprising a channel which includes:
   a tube main body into which the drive shaft is inserted and which protects an outer side of the drive shaft; and
   a fixed portion which is fixed at a proximal end of the tube main body and into which the drive shaft is inserted,
   wherein the tubular portion includes a second adjustment section which is configured to fix the fixed portion of the channel in a state where the distal portion of the drive shaft is arranged at a predetermined position where the driven portion is able to be driven, and a state where a position of the fixed portion of the channel is adjusted to the tubular portion.

8. The mechanism according to claim 7, wherein the second adjustment section is configured to fix the fixed portion in a state where the tube main body of the channel is shortened beyond its natural length.

9. The mechanism according to claim 7, wherein the second adjustment section is configured to move the fixed portion of the channel along the longitudinal direction of the tubular portion, and configured to fix the fixed portion of the channel at a position to which the fixed portion has been moved along the longitudinal direction of the tubular portion.

10. The mechanism according to claim 9, wherein the second adjustment section includes an elongated hole which extends along the longitudinal direction of the tubular portion.

11. The mechanism according to claim 10, wherein:
   the fixed portion of the channel includes screw holes which are apart from each other in the longitudinal direction of the tubular portion, and
   the second adjustment section fixes one of the screw holes of the fixed portion by a screw through the elongated hole of the tubular portion.

12. The mechanism according to claim 7, wherein the second adjustment section fixes the fixed portion of the channel to the tubular portion by a screw.

13. The mechanism according to claim 7, wherein the first adjustment section of the tubular portion is present on a proximal side of the second adjustment section of the tubular portion along the longitudinal direction of the tubular portion.

14. The mechanism according to claim 7, wherein:
   the tubular portion includes:
      a rigid tube having the first adjustment section and the second adjustment section; and
      a flexible tube wherein the distal portion of the drive shaft is arranged on a distal side of the rigid tube,
   the support portion of the drive shaft is movable along the longitudinal direction of the tubular portion in accordance with bending of the flexible tube, and
   the fixed portion of the channel is fixed to the tubular portion irrespective of the bending of the flexible tube.

\* \* \* \* \*